United States Patent
Tadin-Strapps et al.

(10) Patent No.: US 10,004,814 B2
(45) Date of Patent: Jun. 26, 2018

(54) **SYSTEMIC DELIVERY OF MYOSTATIN SHORT INTERFERING NUCLEIC ACIDS (SIN

(56) References Cited

FOREIGN PATENT DOCUMENTS

| WO | 0044914 A1 | 8/2000 |
|---|---|---|
| WO | 200044895 A1 | 8/2000 |
| WO | 0129058 A1 | 4/2001 |
| WO | 0136646 A1 | 5/2001 |
| WO | 2015/070158 A1 | 5/2015 |

OTHER PUBLICATIONS

Bailey, J.L. et al., "Chronic Kidney Disease Causes Defects in Signaling through the Insulin Receptor Substrate-Phosphatidylinositol 3-Kinase-Akt Pathway—Implications for Muscle Atrophy" J. Am. Soc. Nephrol. 17:1388-94 (2006).
Bass et al., "RNA interference: The short answer", Nature, vol. 411, pp. 428-429 (2001).
Chien, P.Y. et al., "Novel cationic cardiolipin analogue-based liposome for efficient DNA and small interfering RNA Delivery in vitro and in vivo" Cancer Gene Ther. 12:321-8 (2005).
Damha et al., "Chemically modified siRNA: Tools and applications", Drug Discovery Today, vol. 13, pp. 843-855 (2008).
Elbashir et al., "Duplexes of 21-nucleotide RNAs mediate RNA interference in cultured mammalian cells", Nature, vol. 411, pp. 494-498 (2001).
Engelen, M.P. et al., "Nutritional depletion in relation to respiratory and peripheral skeletal muscle function in out-patients with COPD" Eur. Respir. J. 7:1793-7 (1994).
Frank-Kamenetsky, M. et al., "Therapeutic RNAi targeting PCSK9 acutely lowers plasma cholesterol in rodents and LDL cholesterol in nonhuman primates", Proc. Natl. Acad. Sci. USA, vol. 105, pp. 11915-11920 (2008).
Grobet, L. et al., "A deletion in the bovine myostatin gene causes the double-muscled phenotype in cattle" Nat. Genet., vol. 17. pp. 71-74 (1997).
Heineke, J. et al., "Genetic Deletion of Myostatin From the Heart Prevents Skeletal Muscle Atrophy in Heart Failure" Circulation 121:419-25 (2010).
International Preliminary Report on Patentability and Written Opinion of the International Searching Authority for application No. PCT/US2014/064837 dated May 17, 2016.
Kambadur, R. et al., "Mutations in myostatin (GDF8) in Double-Muscled Belgian Blue and Piedmontese Cattle", Genome Res. vol. 7, pp. 910-916 (1997).
Kawakami, E. et al., "Atelocollagen-mediated systemic administration of myostatin-targeting siRNA improves muscular atrophy in caveolin-3-deficient mice" Dev. Growth Differ. 53:48-54 (2011).
Kawakami, E. et al., "Local Applications of Myostatin-siRNA with Atelocollagen Increase Skeletal Muscle Mass and Recovery of Muscle Function" EPLoS One 8:e64719 (2013).
Khoury, M. et al., "Efficient New Cationic Liposome Formulation for Systemic Delivery of Small Interfering RNA Silencing Tumor Necrosis Factor in Experimental Arthritis" Arthritis Rheum 54:1867-77 (2006).
Kim, B. et al., "Inhibition of Ocular Angiogenesis by siRNA" Am. J. Pathol. 165:2177-85 (2004).
Kinouchi, N. et al., "Atelocollagen-mediated local and systemic applications of myostatin-targeting siRNA increase skeletal muscle mass" Gene Ther. 15:1126-30 (2008).
Koller et al., "Competition for RISC binding predicts in vitro potency of siRNA", Nucleic Acids Research, vol. 34, pp. 4467-4476 (2006).
Kondo, E. et al., "Tumour lineage-homing cell-penetrating peptides as anticancer molecular delivery systems" Nat. Commun. 3:951 (2012).
Lima et al., "Single-Stranded siRNAs Activate RNAi in Animals," Cell, vol. 150, pp. 883-894 (2012).
Lin, J. et al., "Myostatin Knockout in Mice Increases Myogenesis and Decreases Adipogenesis", Biochem. Biophys. Res. Commun. 291:701-6 (2002).
McPherron, A.C. et al, "Regulation of skeletal muscle mass in mice by a new TGF-beta superfamily member" Nature 387:83-92 (1997).
McPherron, A.C. et al., "Double muscling in cattle due to mutations in the myostatin gene", Proc. Natl. Acad. Sci. USA, vol. 94. pp. 12457-12461, Nov. 1997.
Morissette, M.R., "Myostatin Regulates Cardiomyocyte Growth Through Modulation of Akt Signaling", Circ. Res. vol. 99, pp. 15-24 (2006).
Morrissey, D.V. et al., "Potent and persistent in vivo anti-HBV activity of chemically modified siRNAs" Nat. Biotechnol. 23:1002-7 (2005).
Rodgers, B.D. et al., "Myostatin represses physiological hypertrophy of the heart and excitation-contraction coupling", J. Physiol., vol. 587, pp. 4873-4886 (2009).
Ruegg, M.A. et al., "Molecular Mechanisms and Treatment Options for Muscle Wasting Diseases", Annu. Rev. Pharmacol. Toxicol. 51:373-95 (2011).
Sartori, R.G. et al., "Smad2 and 3 transcription factors control muscle mass in adulthood" Am. J. Physiol. Cell Physiol. 296:C1248-57 (2009).
Schiffelers, R.M. et al., "Cancer siRNA therapy by tumor selective delivery with ligand-targeted sterically stabilized nanoparticle" Nucleic Acids Res. 32:e149 (2004).
Sharma M. et al., "Myostatin, a Transforming Growth Factor-b Superfamily Member, Is Expressed in Heart Muscle and is Upregulated in Cardiomyocytes After Infarct", J. Cell Physiol. 180:1-9 (1999).
Song, E. et al., "Antibody mediated in vivo delivery of small interfering RNAs via cell-surface receptors", Nat. Biotechnol., vol. 23, pp. 709-717 (2005).
Stitt, T.N. et al., "The IGF-1-PI3K-Akt Pathway Prevents Expression of Muscle Atrophy-Induced Ubiquitin Ligases by Inhibiting FOXO Transcription Factors" Mol. Cell 14:395-403 (2004).
Tadin-Strapps, M. et al., "siRNA-induced liver ApoB knockdown lowers serum LDL-cholesterol in a mouse model with human-like serum lipids" J. Lipid Res. 52:1084-97 (2011).
Vaughn et al., "It's a Small RNA World, After All", Science, vol. 309, No. 5740, pp. 1525-1526 (2005).
Weber, H. et al., "Automated rodent in situ muscle contraction assay and myofiber organization analysis in sarcopenia animal models", J. Appl. Physiol., vol. 112, pp. 2087-2098 (2012).
Whittemore, L.A. et al., "Inhibition of myostatin in adult mice increases skeletal muscle mass and strength", Biochem. Biophys. Res. Commun. vol. 300, pp. 965-971 (2003).
Wolfrum, C.S. et al., "Mechanisms and optimization of in vivo delivery of lipophilic siRNAs" Nat. Biotechnol. 25:1149-57 (2007).
Zamore et al., "Ribo-gnome: The Big World of Small RNAs", Science, vol. 309, pp. 1519-1524 (2005).
Zamore et al., "RNAi: Double-Stranded RNA Directs the ATP-Dependent Cleavage of mRNA at 21 to 23 Nucleotide Intervals", Cell, vol. 101, pp. 25-33 (2000).
Zhang, L. et al., "Pharmacological inhibition of myostatin suppresses systemic inflammation and muscle atrophy in mice with chronic kidney disease", Faseb J. 25:1653-63 (2011).
Zhou, X. et al., "Reversal of Cancer Cachexia and Muscle Wasting by ActRIIB Antagonism Leads to Prolonged Survival" Cell 142:531-43 (2010).

* cited by examiner

A.

B.

C.

D.

H.

I.

SYSTEMIC DELIVERY OF MYOSTATIN SHORT INTERFERING NUCLEIC ACIDS (SINA) CONJUGATED TO A LIPOPHILIC MOIETY

CROSS REFERENCE TO RELATED APPLICATIONS

The present application is the U.S. National Phase Application under 35 U.S.C. § 371 of International Application No. PCT/US2014/064837, filed Nov. 10, 2014, which claims the benefit of U.S. Provisional Application No. 61/902,358, filed Nov. 11, 2013, the entire contents of which are incorporated herein by reference.

REFERENCE TO SEQUENCE LISTING

A sequence listing text file is submitted via EFS-Web in compliance with 37 CFR § 1.52(e)(5) concurrently with the specification. The sequence listing has the file name "A2038-7219WO Sequence Listing", was created on Nov. 10, 2014, and is 24,773 bytes in size. The sequence listing is part of the specification and is incorporated in its entirety by reference herein.

BACKGROUND OF THE INVENTION

RNA interference (RNAi) is an evolutionarily conserved cellular mechanism of post-transcriptional gene silencing found in fungi, plants and animals that uses small RNA molecules to inhibit gene expression in a sequence-specific manner. RNAi is controlled by the RNA-induced silencing complex (RISC) that is initiated by short double-stranded RNA molecules in a cell's cytoplasm. The short double-stranded RNA interacts with Argonaute 2 (Ago2), the catalytic component of RISC, which cleaves target mRNA that is complementary to the bound RNA. One of the two RNA strands, known as the guide strand, binds the Ago2 protein and directs gene silencing, while the other strand, known as the passenger strand, is degraded during RISC activation. See, for example, Zamore and Haley, 2005, Science, 309: 1519-1524; Vaughn and Martienssen, 2005, Science, 309: 1525-1526; Zamore et al., 2000, Cell, 101:25-33; Bass, 2001, Nature, 411:428-429; and, Elbashir et al., 2001, Nature, 411:494-498. Single-stranded short interfering RNA has also been shown to bind Ago2 and support cleavage activity (see, e.g., Lima et al., 2012, Cell 150:883-894).

The RNAi machinery can be harnessed to destroy any mRNA of a known sequence. This allows for suppression (knockdown) of any gene from which it was generated, consequently preventing the synthesis of the target protein. Modulation of gene expression through an RNAi mechanism can be used to modulate therapeutically relevant biochemical pathways, including ones which are not accessible through traditional small molecule control.

Chemical modification of nucleotides incorporated into RNAi molecules leads to improved physical and biological properties, such as nuclease stability (see, e.g., Damha et al., 2008, Drug Discovery Today, 13:842-855), reduced immune stimulation (see, e.g., Sioud, 2006, TRENDS in Molecular Medicine, 12:167-176), enhanced binding (see, e.g., Koller, E. et al., 2006, Nucleic Acid Research, 34:4467-4476), and enhanced lipophilic character to improve cellular uptake and delivery to the cytoplasm. Thus, chemical modifications have the potential to increase potency of RNA compounds, allowing lower doses of administration, reducing the potential for toxicity, and decreasing overall cost of therapy.

In recent years, advances in oligonucleotide design and chemical modification types/patterns have resulted in molecules with increased resistance to nuclease-mediated degradation, improved pharmokinetics, increased gene specificity and reduced immunostimulatory responses (Lares, M. R. et al. 2010, Trends Biotechnol. 58:570-9). Despite these major advances, siRNA delivery to a diverse range of tissues remains a major obstacle in vivo. While siRNA delivery in vivo has been achieved in eye, lung, brain, tumor, and muscle by localized delivery (by intraocular, intranasal, intrathecal, intratumoral, and intramuscular injections, respectively), this delivery method is only suitable for target validation studies due to its invasive nature and has limited relevance as a clinical therapy (Golzio, M. et al., 2005, Gene Ther. 12:246-51; Liang, Y. et al., 2010, PLoS One 5:e12860; Reich, S. J. et al., 2003, Mol. Vis. 9:210-6; Tan, P. H. et al., 2005, Gene Ther. 12:59-66; Zhang, X. et al., 2004, J. Biol. Chem. 279:10677-84). A good systemic delivery system is essential to reach certain tissues of interest. Numerous studies have demonstrated systemic and targeted systemic siRNA delivery in vivo through a variety of methods, including cationic lipid and polymers, cholesterol conjugates, cell-penetrating peptides, recombinant viral vectors, small molecule carriers, antibody-linked siRNA and targeting ligands (Frank-Kamenetsky, M. et al., 2008, Proc. Natl. Acad. Sci. USA 105:11915-20; Khoury, M. et al., 2006, Arthritis Rheum. 54:1867-77; Kim, B. et al., 2004, Am. J. Pathol. 165:2177-85; Kondo, E. et al., 2012, Nat. Commun. 3:951; Morrissey, D. V. et al., 2005, Nat. Biotechnol. 23:1002-7; Schiffelers, R. M. et al., 2004, Nucleic Acids Res. 32:e149; Song, E. et al., 2005, Nat. Biotechnol. 23:709-17; Wolfrum, C. S. et al., 2007, Nat. Biotechnol. 25:1149-57). However, systemic siRNA delivery has remained limited to particular tissues, such as liver, tumors, spleen and jejunum (Abrams, M. T. et al., 2010, Mol. Ther. 18:171-80; Chien, P. Y. et al., 2005, Cancer Gene Ther. 12:321-8; Liang, Y. et al., supra; Sorensen, D. R. et al., 2003, J. Mol. Biol. 327:761-6; Tadin-Strapps, M. et al., 2011, J. Lipid Res. 52:1084-97; Wolfrum, C. et al., supra).

Myostatin is an inhibitor of skeletal muscle differentiation and growth. During development it is an inhibitor of myogenesis, while during adulthood its major role is in negatively regulating satellite cell activation and self-renewal. Myostatin is a member of the TGF-β family and acts as a catabolic stimulus through the ActRIIB receptor to induce SMAD2/3/FOXO/NF-κB signaling and muscle fiber atrophy (Sartori, R. G. et al., 2009, Am. J. Physiol. Cell Physiol. 296:C1248-57; Stitt, T. N. et al., 2004, Mol. Cell 14:395-403). Myostatin knockout mice, as well as other mouse models of myostatin inhibition, display increased muscle mass/strength and an attenuated/reversal of a muscle atrophy phenotype in different muscle disease models (Akpan, I. et al., 2009, Int. J. Obes. (Lond) 33:1265-73; Heineke, J. et al., 2010, Circulation 121:419-25; Lin, J. et al., 2002, Biochem. Biophys. Res. Commun. 291:701-6; Zhang, L. 2011, Faseb J. 25:1653-63; Zhou, X. et al., 2010, Cell 142:531-43). Small-interfering RNAs targeting myostatin may have numerous therapeutic applications in the multitude of existing muscle disorders, which range from muscular dystrophy, muscular atrophy in cachexia-inducing diseases, such as cancer, heart disease, chronic obstructive pulmonary disease, sarcopenia, chronic kidney disease, and metabolic diseases, and also in insulin-resistant disorders (Asp, M. L. et al., 2010, Int. J. Cancer 126:756-63; Bailey, J. L. et al., 2006, J. Am. Soc. Nephrol. 17:1388-94; Engelen, M. P. et al., 1994, Eur. Respir. J. 7:1793-7; Ruegg, M. A. et al., 2011, Annu. Rev. Pharmacol. Toxicol. 51:373-95).

To date there has been limited success in siRNA or antisense oligonucleotide (ASO) delivery systemically to muscle, with most reports highlighting muscle targeting by local injection (Gebski, B. L. et al., 2003, *Hum. Mol. Genet.* 12:1801-11; Guess, M. G. et al., 2013, *Skelet. Muscle* 3:19; Laws, N. et al., 2008, *J. Appl. Physiol.* 105:662-8; Tang, Y. et al., 2012, *Mol. Pharmacol.* 82:322-32). Several studies have used electroporation additively with intramuscular (IM) injections to improve the transfer of siRNAs or plasmid vectors into muscle cells (Eefting, D. et al., 2007, *Hum. Gene Ther.* 18:861-9; Golzio, M. et al., 2005, supra; Kishida, T. et al., 2004, *J. Gene Med.* 6:105-10). However, IM injections have a long-standing history for causing pain, local muscle damage and inflammation, which also minimizes their usefulness for therapeutic applications (McMahon, J. M. et al., 1998, *Gene Ther.* 5:1283-90). As an improvement to IM delivery, a model of "local" venous delivery muscle system was developed, which involves the use of a tourniquet to transiently isolate the injection solution in the muscle of the limb, in order to deliver a "high pressure" hydrodynamic injection of a luciferase pDNA vector to muscle in rats, dogs and monkeys (Hagstrom, J. E. et al., 2004, *Mol. Ther.* 10:386-98). Although it showed successful delivery into multiple muscle groups in the limb and the ability for multiple dosing, delivery efficiency was low and it is still an invasive technique that requires a high degree of injection skill.

In recent years, the use of the carrier polymer, atelocollagen, has been used for delivery of nucleic acids (siRNA, ASOs and plasmids) and negatively-charged proteins. Recent studies shows both local and systemic delivery of an atelocollagen/siRNA complex to muscle in a model of Duchenne muscular dystrophy (DMD) (Kawakami, E. et al., 2013, *PLoS One* 8:e64719; Kawakami, E. et al., 2011, *Dev. Growth Differ.* 53:48-54; Kinouchi, N. et al., 2008, *Gene Ther.* 15:1126-30).

There continues to be a need to develop therapies that can easily and non-invasively deliver nucleic acids to the muscle, which could have the potential for use in the future treatment of a variety of muscle disorders, such as muscular atrophic diseases, muscular dystrophy, and type II diabetes.

SUMMARY OF THE INVENTION

The present invention provides methods for delivering to a subject small nucleic acid molecules capable of mediating RNA interference and reducing the expression of myostatin. The small nucleic acid molecules of the invention are more specifically referred to herein as short interfering nucleic acid (siNA) molecules. The siNA molecules that are delivered as per the methods disclosed target a myostatin gene and are conjugated to a lipophilic moiety, such as cholesterol (i.e., myostatin siNA conjugates). Once delivered to their site of action (e.g., muscle cells that express myostatin), the myostatin siNA conjugates act to inhibit or down regulate myostatin gene expression by causing destruction of a myostatin gene. By reducing the expression of a myostatin gene and, in turn, reducing the level of myostatin protein, the methods of the invention have the potential of enhancing muscle mass and/or function. Thus, use of the disclosed methods is indicated, for example, for treating musculoskeletal diseases/disorders and diseases/disorders that result in conditions in which muscle is adversely affected, such as neurodegenerative diseases/disorders, sarcopenia, cachexia, obesity, Type-II diabetes, HIV/AIDS and cancer. The methods of the invention are also useful, for example, for enhancing muscle mass and/or function in livestock including, but not limited to, cattle, pigs and fowl.

An embodiment of the present invention relates to methods of delivering to the muscle of a subject a short interfering nucleic acid (siNA) molecule, or pharmaceutical compositions thereof, that targets a myostatin gene comprising the step of systemically administering to said subject a conjugate of said siNA, wherein said conjugate comprises the siNA molecule linked to a lipophilic moiety (e.g., cholesterol). Thus, the present invention relates to methods of delivering to the muscle of a subject myostatin siNA conjugates, or pharmaceutical compositions thereof, via systemic administration. The myostatin siNA conjugates that are systemically administered to the subject are delivered to muscle that expresses myostatin. Once delivered to the muscle, the myostatin siNA conjugate reduces myostatin expression by an RNA interference mechanism. Thus, the present invention relates to methods of delivering to the muscle of a subject a myostatin siNA conjugate, or a pharmaceutical composition thereof, comprising systemically administering the myostatin siNA conjugate to said subject in an amount effective to modulate (e.g., inhibit or down-regulate) myostatin expression in said muscle, wherein said myostatin siNA conjugate comprises an siNA molecule that targets a myostatin gene expressed by said subject linked to a lipophilic moiety (e.g., cholesterol), and wherein said myostatin siNA conjugate mediates RNA interference.

An embodiment of the present invention relates to methods of modulating (e.g., inhibiting or down-regulating) in vivo expression of a myostatin gene in a subject comprising introducing to said subject an effective amount of a myostatin siNA conjugate, or a pharmaceutical composition thereof, by systemic administration, wherein the siNA conjugate comprises a siNA molecule that targets a myostatin gene expressed by said subject linked to a lipophilic moiety (e.g., cholesterol), and wherein the siNA conjugate mediates RNA interference. Another embodiment relates to methods of modulating (e.g., inhibiting or down-regulating) in vivo expression of a myostatin gene in a subject comprising delivering to the muscle of said subject an effective amount of a myostatin siNA conjugate, or a pharmaceutical composition thereof, by introducing the siNA conjugate to said subject by systemic administration, wherein the siNA conjugate comprises a siNA molecule that targets a myostatin gene expressed by said subject linked to a lipophilic moiety (e.g., cholesterol), and wherein the siNA conjugate mediates RNA interference. Thus, the present invention relates to methods of modulating in vivo expression of a myostatin gene in a subject comprising systemically administering an effective amount of an siNA conjugate, or a pharmaceutical composition thereof, to said subject, wherein the siNA conjugate comprises an siNA molecule that targets a myostatin gene expressed by said subject linked to a lipophilic moiety, and wherein said siNA conjugate mediates RNA interference. The myostatin siNA conjugates that are systemically administered to the subject are delivered to muscle that expresses myostatin and, by an RNA interference mechanism, inhibits or down-regulates the expression of a myostatin gene in the muscle.

A further aspect of the invention includes myostatin siNA conjugates for use to modulate in vivo expression of a myostatin gene expressed by a subject (i.e., a human or animal). Another embodiment relates to the use of a conjugate comprising an siNA molecule that targets a myostatin gene and a lipophilic moiety (e.g., cholesterol), for the manufacture of a medicament for modulating in vivo expression of a myostatin gene expressed by a subject, which comprises systemic administration of said conjugate, or a pharmaceutical composition thereof, to said subject.

Another embodiment of the present invention provides methods for enhancing muscle mass in a subject comprising reducing myostatin levels in said subject by introducing to said subject an effective amount of a myostatin siNA conjugate, or a pharmaceutical composition thereof, by systemic administration, wherein the siNA conjugate comprises an siNA molecule that targets a myostatin gene expressed by said subject linked to a lipophilic moiety (e.g., cholesterol), and wherein the siNA conjugate mediates RNA interference. Another embodiment relates to methods for enhancing muscle mass in a subject comprising reducing myostatin levels in said subject by delivering to the muscle of said subject an effective amount of a myostatin siNA conjugate, or a pharmaceutical composition thereof, by introducing the siNA conjugate to said subject by systemic administration, wherein the siNA conjugate comprises an siNA molecule that targets a myostatin gene expressed by said subject linked to a lipophilic moiety (e.g., cholesterol), and wherein the siNA conjugate mediates RNA interference. The phrase "reducing myostatin levels," as used herein, refers to either reducing expression of a myostatin gene or reducing myostatin protein levels. The myostatin siNA conjugates that are systemically administered to the subject are delivered to muscle that expresses myostatin and, by an RNA interference mechanism, inhibits or down-regulates the expression of a myostatin gene in the muscle. The decrease in myostatin expression results in an increase in the muscle mass of the subject. The terms "muscle enhancement" and "enhancing muscle" are intended to be interchangeable herein and include, but are not limited to, inducement of hyperplasia (increased muscle fiber number), inducement of hypertrophy (increased muscle fiber diameter) or both. The increase can be in type 1 and/or type 2 muscle fibers. This aspect of the invention further relates to methods of regenerating injured musculoskeletal tissue in a subject in need thereof by systemically delivering myostatin siNA conjugates, or pharmaceutical compositions thereof, described herein.

A further aspect of the invention includes myostatin siNA conjugates for use to enhance muscle mass and/or to regenerate injured musculoskeletal tissue in a subject. Another embodiment relates to the use of a conjugate comprising an siNA molecule that targets a myostatin gene linked to a lipophilic moiety (e.g., cholesterol), for the manufacture of a medicament for enhancing muscle mass and/or regenerating injured musculoskeletal tissue in a subject, which comprises systemic administration of said conjugate, or a pharmaceutical composition thereof, to said subject.

Another embodiment of the present invention provides methods for enhancing muscle performance in a subject comprising reducing myostatin levels in said subject by introducing to said subject an effective amount of a myostatin siNA conjugate, or a pharmaceutical composition thereof, by systemic administration, wherein the siNA conjugate comprises an siNA molecule that targets a myostatin gene expressed by said subject linked to a lipophilic moiety (e.g., cholesterol), and wherein the siNA conjugate and mediates RNA interference. Another embodiment relates to methods for enhancing muscle performance in a subject comprising reducing myostatin levels in said subject by delivering to the muscle of said subject an effective amount of a myostatin siNA conjugate, or a pharmaceutical composition thereof, by introducing the siNA conjugate to said subject by systemic administration, wherein the siNA conjugate comprises an siNA molecule that targets a myostatin gene expressed by said subject linked to a lipophilic moiety (e.g., cholesterol), and wherein the siNA conjugate mediates RNA interference. The myostatin siNA conjugates that are systemically administered to the subject are delivered to muscle that expresses myostatin and, by an RNA interference mechanism, inhibits or down-regulates the expression of a myostatin gene in the muscle. The decrease in myostatin expression results in an increase muscle performance in the subject. "Enhanced muscle performance" includes, but is not limited to, one or more of decreased atrophy, increased muscle endurance and increased overall muscle strength (e.g., increased contractile force). A further aspect of the invention includes myostatin siNA conjugates for use to enhance muscle performance in a subject.

Another embodiment of the invention relates to methods of treating musculoskeletal diseases or disorders and/or diseases or disorders that result in conditions in which muscle is adversely affected (e.g., muscle weakness, muscle atrophy) in a subject in need thereof comprising the step of reducing myostatin levels in said subject by introducing to said subject an effective amount of a myostatin siNA conjugate, or a pharmaceutical composition thereof, by systemic administration, wherein the siNA conjugate comprises an siNA molecule that targets a myostatin gene expressed by said subject linked to a lipophilic moiety (e.g., cholesterol), and wherein the siNA conjugate mediates RNA interference. A further embodiment of the invention relates to methods of treating musculoskeletal diseases or disorders and/or diseases or disorders that result in conditions in which muscle is adversely affected (e.g., muscle weakness, muscle atrophy) in a subject in need thereof comprising the step of reducing myostatin levels in said subject by delivering to the muscle of said subject an effective amount of a myostatin siNA conjugate, or a pharmaceutical composition thereof, by systemic administration, wherein the siNA conjugate comprises an siNA molecule that targets a myostatin gene expressed by said subject linked to a lipophilic moiety (e.g., cholesterol), and wherein the siNA conjugate mediates RNA interference. The myostatin siNA conjugates that are systemically administered to the subject are delivered to muscle that expresses myostatin and, by an RNA interference mechanism, inhibits or down-regulates the expression of a myostatin gene in the muscle. The decrease in myostatin expression results in an increased muscle mass and/or enhanced muscle performance in the subject.

A further aspect of the invention includes myostatin siNA conjugates for use to treat musculoskeletal diseases or disorders and/or diseases or disorders that result in conditions in which muscle is adversely affected in a subject. Another embodiment relates to the use of a conjugate comprising an siNA molecule that targets a myostatin gene linked to a lipophilic moiety (e.g., cholesterol), for the manufacture of a medicament for treating musculoskeletal diseases or disorders and/or diseases or disorders that result in conditions in which muscle is adversely affected in a subject, which comprises systemic administration of said conjugate, or a pharmaceutical composition thereof, to said subject.

The methods of the present invention can be performed on a subject to which nucleic acid molecules can be systemically administered. The term "subject" as used herein is intended to include human and non-human animals. Non-human animals include all vertebrates, for example, mammals and non-mammals, such as non-human primates, sheep, dogs, cats, cows, horses, chickens, amphibians, and reptiles. In one embodiment, the methods of the present invention are performed on a mammal. In another embodiment, the methods of the present invention are performed on livestock. In another embodiment, the methods of the present invention are performed on humans. In a further embodiment, the human is diagnosed with musculoskeletal disease. The term "subject" is also intended to include an embryo, including a chicken embryo contained within an egg.

An embodiment of the present invention relates to a conjugate comprising an siNA molecule that targets a myostatin gene and a lipophilic moiety (e.g., cholesterol). The myostatin siNA conjugates of the invention may be used in a method of treatment of a subject by therapy, which comprises systemic administration of said conjugate, or a pharmaceutical composition thereof, to said subject. A further embodiment relates to the use of a conjugate comprising an siNA molecule that targets a myostatin gene and a lipophilic moiety (e.g., cholesterol), for the manufacture of a medicament for treating a subject, which comprises systemic administration of said conjugate, or a pharmaceutical composition thereof, to said subject.

An embodiment of the present invention relates to a conjugate comprising an siNA molecule that targets a myostatin gene and a lipophilic moiety (e.g., cholesterol), for use in a method of treatment of a subject by therapy, wherein the conjugate is formulated for systemic administration. A further embodiment relates to the use of a conjugate comprising an siNA molecule that targets a myostatin gene and a lipophilic moiety (e.g., cholesterol), for the manufacture of a medicament for treating a subject, wherein the conjugate is formulated for systemic administration.

The myostatin siNA conjugates of the present invention that are delivered by the disclosed methods comprise a myostatin siNA molecule linked to a lipophilic moiety. The myostatin siNA conjugates delivered by the methods of the present invention are not formulated with lipid formulations that form liposomes. While not wishing to be bound by a particular theory, it is believed the attachment of a lipophilic moiety to the myostatin siNA molecule increases the lipophilicity of the siNA molecule, enhancing the entry of the siNA molecule into muscle cells. Examples of lipophilic moieties that can be linked to the myostatin siNA molecule include, but are not limited to cholesterol, oleic acid, stearic acid, palmitic acid, myristic acid, linoleic acid, oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, O3-(oleoyl)lithocholic acid, O3-(oleoyl)cholenic acid, dimethoxytrityl, or phenoxazine. A preferred lipophilic moiety is cholesterol.

The lipophilic moiety is attached to the myostatin siNA molecule through linkage to a terminus of the siNA molecule (e.g., the 3' or 5' end of the sense strand of the siNA molecule) or through linkage to an internal nucleotide of the siNA molecule. In one embodiment, the lipophilic moiety is attached to the 3' end of the passenger strand (sense strand) of a double-stranded myostatin siNA molecule. In one embodiment, the lipophilic moiety is attached to the 5' end of the passenger strand of a double-stranded myostatin siNA molecule. In a further embodiment, the lipophilic moiety is attached to the 3' end of the guide strand (antisense strand) of a myostatin siNA molecule. In a further embodiment, a myostatin siNA conjugate contains more than one attached lipophilic moiety (e.g., a lipophilic moiety attached to both the 3' and the 5' end of the passenger strand; a lipophilic moiety attached to the 3' end of the guide strand and the 5' end of the passenger strand). In this aspect of the invention, the lipophilic moieties can be the same or different.

The present invention further provides siNA molecules useful for modulating the expression of myostatin genes and to which a lipophilic moiety can be attached to form the myostatin siNA conjugates described herein. The siNA portion of the myostatin siNA conjugates that are delivered by the methods of the present invention can be single- or double-stranded small interfering nucleic acid molecules and can take different oligonucleotide forms, including but not limited to short interfering RNA (siRNA), double-stranded RNA (dsRNA) and short hairpin RNA (shRNA) molecules. In one embodiment, the myostatin siNA molecules are double-stranded siNA molecules comprising a sense and an antisense strand. The antisense strand comprises a sequence that is complementary to a portion of a myostatin target RNA sequence, and the sense strand is complementary to at least part of the antisense strand. The double-stranded myostatin siNA molecules delivered by the methods of the present invention can be symmetric or asymmetric. In another aspect, the myostatin siNA molecules are single-stranded siNA molecules, wherein the single oligonucleotide strand (the antisense strand) comprises a sequence that is complementary to at least part of a myostatin target RNA sequence. The siNA portion of the myostatin siNA conjugates that are delivered by the methods of the present invention inhibit myostatin gene expression in a subject via an RNA interference (RNAi) mechanism.

The myostatin siNA conjugates described herein are directed to a myostatin gene that can be derived from any of a number of animal species, including but not limited humans, cattle, swine, fowl and rodent. In one embodiment, the myostatin gene is a human myostatin RNA. In another embodiment, the myostatin gene is a cattle myostatin RNA. In another embodiment, the myostatin gene is a swine myostatin RNA. In a further embodiment, the myostatin gene is a fowl myostatin RNA (e.g., chicken, turkey). In a further embodiment, the myostatin gene is a rodent myostatin RNA (e.g., mouse).

In certain embodiments, the siNA molecules of the siNA portion of the myostatin siNA conjugates that are delivered by the methods of the present invention comprise an antisense strand having at least 15 nucleotides with sequence complementarity to a myostatin gene sequence. In other embodiments, the antisense strand of an siNA molecule delivered by the methods of the present invention is about 15 to 30 nucleotides in length. In further embodiments, a double-stranded siNA molecule delivered by the methods of the present invention comprises a sense strand and an antisense strand, wherein each strand is independently about 15 to 30 nucleotides in length.

In one embodiment, the siNA portion of the siNA conjugates of the invention are double-stranded siNA molecules that modulate the expression of a myostatin gene, wherein the siNA molecule comprises a sense strand and an antisense strand, wherein each strand is independently 15 to 30 nucleotides in length, and wherein the antisense strand comprises at least 15 nucleotides having sequence complementary to any of:

```
                                              (SEQ ID NO: 1)
         5'- AUGGCAAAGAACAAAUAAU -3';

(SEQ ID NO: 2)
         5'- GGCAAAGAACAAAUAAUAU -3';

(SEQ ID NO: 3)
         5'- ACUCCAGAAUAGAAGCCAU -3';
      or (SEQ ID NO: 4)
         5'- UUUGGAAGAUGACGAUUAU -3'.
```

In one embodiment, the "at least 15 nucleotides" are 15 contiguous nucleotides.

In some embodiments, the antisense strand of the siNA molecule portion of the myostatin siNA conjugates of the invention comprises at least 15 nucleotides having sequence identity to any of:

```
                                       (SEQ ID NO: 18)
5'- AUUAUUUGUUCUUUGCCAU -3';

(SEQ ID NO: 19)
5'- AUAUUAUUUGUUCUUUGCC -3';

(SEQ ID NO: 20)
5'- AUGGCUUCUAUUCUGGAGU -3';
or (SEQ ID NO: 21)
5'- AUAAUCGUCAUCUUCCAAA -3'.
```

In one embodiment, the "at least 15 nucleotides" are 15 contiguous nucleotides. Thus, the antisense strand of the siNA molecule comprises at least a 15 nucleotide sequence of any of SEQ ID NOs: 18-21.

In some embodiments, the sense strand of the siNA molecule portion of the myostatin siNA conjugates of the invention comprises at least 15 nucleotides having sequence identity to any of:

```
                                       (SEQ ID NO: 1)
5'- AUGGCAAAGAACAAAUAAU -3';

(SEQ ID NO: 2)
5'- GGCAAAGAACAAAUAAUAU -3';

(SEQ ID NO: 3)
5'- ACUCCAGAAUAGAAGCCAU -3';
or (SEQ ID NO: 4)
5'- UUUGGAAGAUGACGAUUAU -3'.
```

In one embodiment, the "at least 15 nucleotides" are 15 contiguous nucleotides. Thus, the sense strand of the siNA molecule comprises at least a 15 nucleotide sequence of any of SEQ ID NOs: 1-4.

In some embodiments, the siNA molecule portion of the myostatin siNA conjugates of the invention comprises at least a 15 nucleotide sequence of both SEQ ID NO: 1 and 18; or both SEQ ID NO: 2 and 19; or both SEQ ID NO: 3 and 20; or both SEQ ID NO: 4 and 21. In another embodiment, the siNA molecule portion of the myostatin siNA conjugates comprises any of the following double-stranded molecules:

```
                                       (SEQ ID NO: 1)
5'- AUGGCAAAGAACAAAUAAU -3'
and
                                       (SEQ ID NO: 18)
5'- AUUAUUUGUUCUUUGCCAU -3';

(SEQ ID NO: 2)
5'- GGCAAAGAACAAAUAAUAU -3'
and
                                       (SEQ ID NO: 19)
5'- AUAUUAUUUGUUCUUUGCC -3';

(SEQ ID NO: 3)
5'- ACUCCAGAAUAGAAGCCAU -3'
and
```

```
                                       (SEQ ID NO: 20)
5'- AUGGCUUCUAUUCUGGAGU -3';
or
                                       (SEQ IN NO: 4)
5'- UUUGGAAGAUGACGAUUAU -3'
and
                                       (SEQ ID NO: 21)
5'- AUAAUCGUCAUCUUCCAAA -3'.
```

In some embodiments of the invention, the siNA molecule is linked to a lipophlic moiety. In anther embodiment, the lipophilic moiety is cholesterol. In another embodiment, the lipophilic moiety is attached to 3' end of the siNA molecule. In another embodiment, the lipophilic moiety is attached to 5' end of the siNA molecule. In another embodiment, a lipophilic moiety is attached to each of the 3' and the 5' ends of the siNA molecule.

In some embodiments of the invention, all of the nucleotides of siNA molecule portion of the myostatin siNA conjugates of the invention are unmodified. In other embodiments, the siNA molecules delivered by the methods of the present invention further comprise one or more nucleotides in either one or both strands of the molecule that are chemically-modified. Modifications include nucleic acid sugar modifications, base modifications, backbone (internucleoside linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In certain instances the purines are unmodified in one or both strands, while the pyrimidines in one or both strands are modified. In certain other instances, the pyrimidines are unmodified in one or both strands, while the purines in one or both strands are modified. In some instances, at least one modified nucleotide is a 2'-deoxy-2'-fluoro nucleotide, a 2'-deoxy nucleotide, or a 2'-O-alkyl nucleotide. In some instances, at least 5 or more of the pyrimidine nucleotides in one or both strands are either all 2'-deoxy-2'-fluoro or all 2'-O-methyl pyrimidine nucleotides. In some instances, at least 5 or more of the purine nucleotides in one or both strands are either all 2'-deoxy-2'-fluoro or all 2'-O-methyl purine nucleotides. In certain instances, wherein the siNA molecules comprise one or more modifications as described herein, the nucleotides at positions 1, 2, and 3 at the 5' end of the guide (antisense) strand are unmodified. In certain embodiments, the siNA molecules delivered by the methods of the present invention comprise one or more modified internucleoside linking groups. In certain embodiments, each internucleoside linking group is, independently, a phosphodiester or phosphorothioate linking group.

In certain embodiments, the siNA molecule portion of the myostatin siNA conjugates of the invention have 3' overhangs of one, two, three or four nucleotide(s) on one or both of the strands. In other embodiments, the double-stranded siNA molecules lack overhangs (i.e., have blunt ends). Preferably, the siNA molecule has 3' overhangs of two nucleotides on both the sense and antisense strands. The overhangs can be modified or unmodified. Examples of modified nucleotides in the overhangs include, but are not limited to, 2'-O-alkyl nucleotides, 2'-deoxy-2'-fluoro nucleotides, locked nucleic acid (LNA) nucleotides, or 2'-deoxy nucleotides. The overhanging nucleotides in the antisense strand can comprise nucleotides that are complementary to nucleotides in the myostatin target sequence. Likewise, the overhangs in the sense strand can comprise nucleotides that are present in the myostatin target sequence. In certain instances, the siNA molecules have two 3' overhanging nucleotides on the antisense strand that are 2'-O-alkyl (e.g., 2'-O-methyl) nucleotides and two 3' overhanging nucleotides on the sense strand that are 2'-deoxy nucleotides. In other instances, the siNA molecules have two 3' overhanging nucleotides that are 2'-O-alkyl (e.g., 2'-O-methyl) nucleotides on both the antisense strand and the sense strand. In certain embodiments, the 2'-O-alkyl nucleotides are 2'-O-methyl uridine nucleotides. In certain instances, the 3' overhangs also comprise one or more phosphorothioate linkages between nucleotides of the overhang.

In some embodiments, the siNA molecule portion of the myostatin siNA conjugates of the invention have one or more terminal caps (also referred to herein as "caps"). A cap may be present at the 3'-terminus (3'-cap) of the antisense strand (guide strand), at the 5'-terminus (5'-cap) of the sense strand (passenger strand), and/or at 3'-terminus (3'-cap) of the sense strand (passenger strand). The lipophilic moiety may be attached to the same terminus of the siNA molecule that contains a terminal cap.

In some embodiments, the siNA molecule portion of the myostatin siNA conjugates of the invention are phosphorylated at the 5' end of the antisense strand. The phosphate group can be a phosphate, a diphosphate or a triphosphate.

In certain embodiments of this aspect of the invention, the siNA portion of the myotstatin siNA conjugates of the invention are double-stranded siNA molecules wherein the antisense and/or sense strand comprises at least one nucleotide sequence selected from SEQ ID NOs: 5-12, provided in Table 3. In a further embodiment, the siNA portion of the myostatin siNA conjugates of the invention comprises any of the following double-stranded molecules: SEQ ID NO: 5 and 6; SEQ ID NO: 7 and 8; SEQ ID NO: 9 and 10; or SEQ ID NO: 11 and 12.

The present invention further provides compositions comprising the myostatin siNA conjugates described herein with, optionally, a pharmaceutically acceptable carrier or diluent. The methods of the present invention include delivery of compositions comprising the myostatin siNA conjugates described herein with a pharmaceutically acceptable carrier or diluent, wherein said compositions are formulated for systemic administration.

These and other aspects of the invention will be apparent upon reference to the following Detailed Description and attached figures. Moreover, it is contemplated that any method or composition described herein can be implemented with respect to any other method or composition described herein and that different embodiments may be combined.

Additionally, patents, patent applications and other documents are cited throughout the specification to describe and more specifically set forth various aspects of this invention. Each of these references cited herein is hereby incorporated by reference in its entirety, including the drawings.

DETAILED DESCRIPTION OF THE INVENTION

A. Terms and Definitions

Figures 1A, 1B:
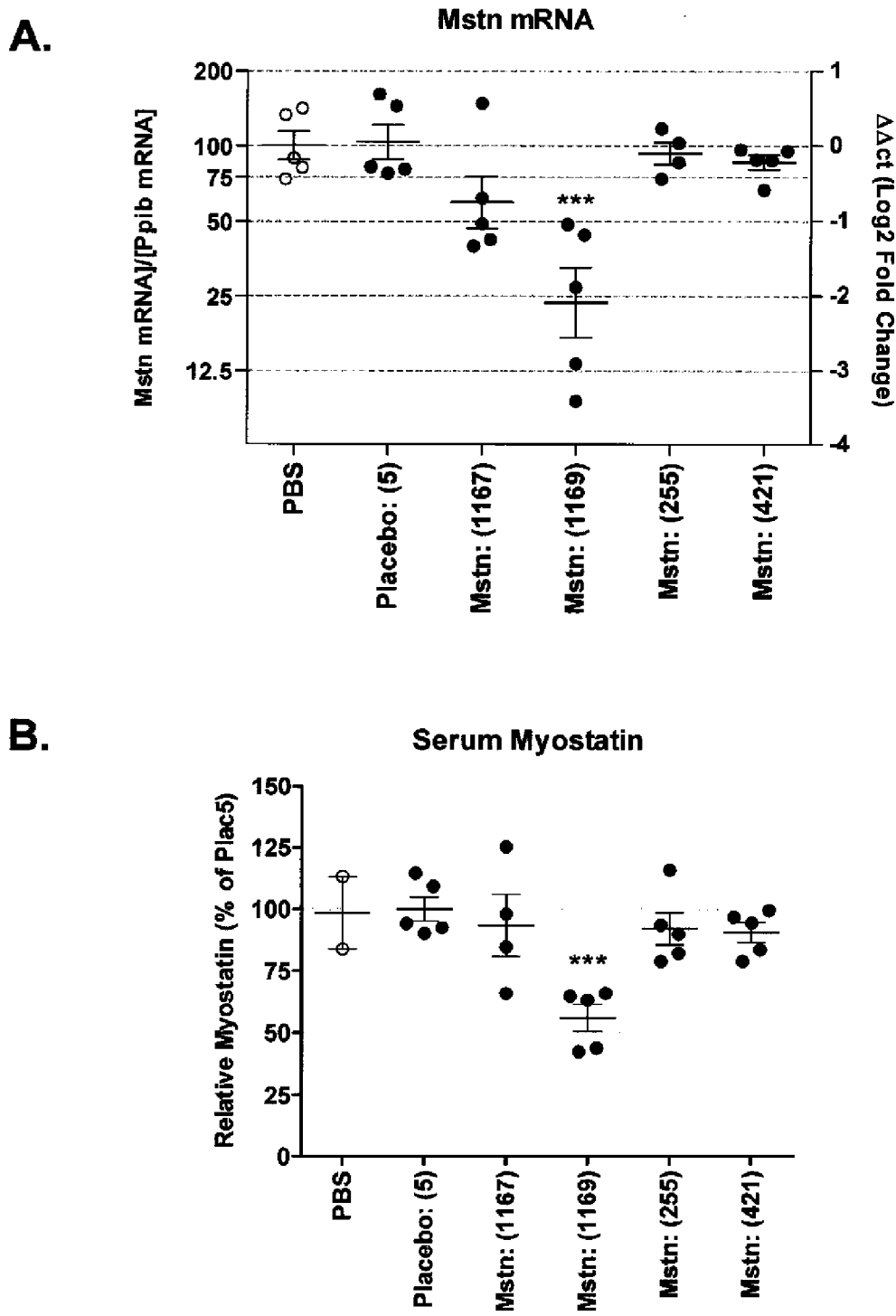
FIG. 1: In vivo screen of Mstn-cholesterol conjugates. Four Mstn-cholesterol siRNAs (•), PBS (○), and Placebo 5 non-targeting control (•) were screened in CD-1 mice (n=5) at a 15 mpk dose by i.v. injection. (A) Mstn mRNA expression was determined based on ΔΔCt calculations, relative to PBS, in gastrocnemius muscle 3 days post-injection. (B) Mstn protein levels were measured in serum 3 days after dosing. ***, P<0.001 (by one-way ANOVA).

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as one tenth and one hundredth of an integer), unless otherwise indicated.

"About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The phrases "2'-modified nucleotide," "2'-substituted nucleotide" or a nucleotide having a modification at the "2'-position" of the sugar moiety, as used herein, generally refer to nucleotides comprising a substituent at the 2' carbon position of the sugar component that is other than H or OH. 2'-modified nucleotides include, but are not limited to, bicyclic nucleotides wherein the bridge connecting two carbon atoms of the sugar ring connects the 2' carbon and another carbon of the sugar ring; and nucleotides with non-bridging 2'substituents, such as allyl, amino, azido, thio, O-allyl, $OC_{1-10}$ alkyl, —OCF3, O—$(CH_2)_2$—O—$CH_3$, 2'-O $(CH_2)_2SCH_3$, O—$(CH_2)_2$—O—$N(R_m)(R_n)$, or O—$CH_2$—C (=O)—$N(R_m)(R_n)$, where each $R_m$ and $R_n$ is, independently, H or substituted or unsubstituted $C_{1-10}$ alkyl. 2'-modified nucleotides may further comprise other modifications, for example at other positions of the sugar and/or at the nucleobase. The phrases "3'-modified nucleotide," "3'-substituted nucleotide" or a nucleotide having a modification at the "3'-position" of the sugar moiety generally refers to a nucleotide comprising a modification, including a substituent, at the 3' carbon position of the sugar component.

The term "abasic" as used herein refers to its meaning as is generally accepted in the art. The term generally refers to sugar moieties lacking a nucleobase or having a hydrogen atom (H) or other non-nucleobase chemical groups in place of a nucleobase at the 1' position of the sugar moiety, see for example Adamic et al., U.S. Pat. No. 5,998,203. In one embodiment, an siNA molecule of the invention may contain an abasic moiety, wherein the abasic moiety is ribose, deoxyribose, or dideoxyribose sugar.

The term "acyclic nucleotide" as used herein refers to its meaning as is generally accepted in the art. The term generally refers to any nucleotide having an acyclic ribose sugar, for example where any of the ribose carbon/carbon or carbon/oxygen bonds are independently or in combination absent from the nucleotide.

If no number of carbon atoms is specified, the term "alkyl" refers to a saturated aliphatic hydrocarbon group, branched or straight-chain, containing from 1 to 10 carbon atoms. An alkyl group can have a specific number of carbon atoms. For example, $C_1$-$C_{10}$, as in "$C_1$-$C_{10}$ alkyl" or "$C_{1-10}$ alkyl," is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

The term "antisense region" as used herein refers to its meaning as is generally accepted in the art. With reference to the siNA molecules delivered by the methods of the present invention, the term refers to a nucleotide sequence of an siNA molecule having complementarity to a myostatin RNA. In addition, the antisense region of an siNA molecule comprises a nucleic acid sequence having complementarity to a sense region of the siNA molecule. In one embodiment, the antisense region of an siNA molecule is referred to as the antisense strand or guide strand.

The term "biodegradable" as used herein refers to its meaning as is generally accepted in the art. The term generally refers to degradation in a biological system, for example, enzymatic degradation or chemical degradation.

The term "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The term "blunt end" as used herein refers to its meaning as is generally accepted in the art. With reference to nucleic acid molecules of the invention, the term refers to termini of a double-stranded siNA molecule having no overhanging nucleotides. An siNA duplex molecule of the invention can comprise blunt ends at one or both termini of the duplex, such as termini located at the 5'-end of the antisense strand, the 5'-end of the sense strand, or both termini of the duplex.

The term "cap" (also referred to herein as "terminal cap") as used herein refers to its meaning as is generally accepted in the art. With reference to exemplary nucleic acid molecules of the invention, the term refers to a moiety, which can be a chemically-modified nucleotide or a non-nucleotide, incorporated at one or more termini of the nucleic acid molecules of the invention. These terminal modifications may protect the nucleic acid molecule from exonuclease degradation and may help in delivery and/or localization of the nucleic acid molecule within a cell. The cap can be present at a 5'-terminus (5'-cap) or 3'-terminus (3'-cap) of a strand of the nucleic acid molecules of the invention, or can be present on both termini. For example, a cap can be present at the 5'-end, 3'-end and/or 5' and 3'-ends of the sense strand of a nucleic acid molecule of the invention. Additionally, a cap can be present at the 3'-end of the antisense strand of a nucleic acid molecule of the invention. In non-limiting examples, a 5'-cap includes, but is not limited to, LNA; glyceryl; inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide; 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of a 3'-cap include, but are not limited to, LNA; glyceryl; inverted deoxy abasic residue (moiety); 4',5'-methylene nucleotide; 1-(beta-D-erythrofuranosyl) nucleotide; 4'-thio nucleotide; carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate; phosphorothioate and/or phosphorodithioate; bridging or non-bridging methylphosphonate; and 5'-mercapto moieties (for more details see Beaucage and Iyer, 1993, *Tetrahedron* 49, 1925; incorporated by reference herein). In one embodiment, siNA molecules of the present invention contain a vinyl phosphate 5' terminal cap, wherein carbon 5 of the sugar ring contains the following substituent (=CH)—P(=O)(OH)$_2$.

The term "cell" as used herein refers to its meaning as is generally accepted in the art. The term is used herein in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be of somatic or germ line origin, totipotent or pluripotent, dividing or non-dividing. The cell can also be derived from or can comprise a gamete or embryo, a stem cell, or a fully differentiated cell. The cell can be a muscle cell.

The phrases "chemically-modified nucleotide," "modified nucleotide" or, when used in reference to nucleotides within the myostatin siNA molecules described herein, "chemical modification," refer to a nucleotide that contains a modification in the chemical structure of the heterocyclic base moiety, sugar and/or phosphate of the unmodified (or natural) nucleotide as is generally known in the art (i.e., at least one modification compared to a naturally occurring RNA or DNA nucleotide). In certain embodiments, the terms can refer to certain forms of RNA that are naturally occurring in certain biological systems, for example 2'-O-methyl modifications or inosine modifications. A modified nucleotide includes abasic nucleotides. Modified nucleotides include nucleotides with a modified sugar ring or sugar surrogate. Modified heterocyclic base moieties include without limitation, universal bases, hydrophobic bases, promiscuous bases, size-expanded bases, and fluorinated bases as defined herein. Certain of these nucleobases are particularly useful for increasing the binding affinity of the siNA molecules as provided herein. These include 5-substituted pyrimidines, 6-azapyrimidines and N-2, N-6 and 0-6 substituted purines, including 2-aminopropyladenine, 5-propynyluracil and 5-propynylcytosine. A modified internucleoside linkage refers to any internucleoside linkage other than a naturally occurring internucleoside linkage. Non-limiting examples of modified nucleotides are described herein and in U.S. application Ser. No. 12/064,014 (published as US 20090176725).

The terms "complementarity" or "complementary" as used herein refers to its meaning as is generally accepted in the art. The terms generally refer to the formation or existence of hydrogen bond(s) between one nucleic acid sequence and another nucleic acid sequence by either traditional Watson-Crick or other non-traditional types of bonding as described herein. In reference to the nucleic acid molecules delivered by the methods of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol. LII* pp. 123-133; Frier et al., 1986, *Proc. Nat. Acad. Sci. USA* 83:9373-9377; Turner et al., 1987, *J. Am. Chem. Soc.* 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, 10 or more mismatches, non-nucleotide linkers, or non-based paired nucleotides) within the nucleic acid molecule, which can result in bulges, loops, or overhangs between the sense strand or sense region and the antisense strand or antisense region of a nucleic acid molecule or between the antisense strand or antisense region of a nucleic acid molecule and a corresponding target nucleic acid molecule. Such partial complementarity can be represented by a % complementarity that is determined by the number of non-base paired nucleotides, e.g., about 50%, 60%, 70%, 80%, 90% etc. depending on the total number of nucleotides involved. Such partial complementarity is permitted to the extent that the nucleic acid molecule (e.g., siNA) maintains its function, for example the ability to mediate sequence specific RNAi.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The term "conjugate" refers to an atom or group of atoms bound to an siNA molecule delivered by the methods of the invention. In general, conjugate groups modify one or more properties of the molecule to which they are attached, including, but not limited to pharmacodynamics, pharmacokinetic, binding, absorption, cellular distribution, cellular uptake, charge and clearance. Conjugate groups are routinely used in the chemical arts and are linked directly or via an optional linking moiety or linking group to the parent compound, such as an siNA molecule. The siNA conjugates used in the methods of the present invention comprise an siNA molecule that targets myostatin RNA linked to a lipophilic moiety, such as cholesterol. In certain embodiments, the lipophilic moiety is attached to a 3' or 5' terminal nucleotide or to an internal nucleotide of a myostatin siNA molecule. As used herein, "conjugate linking group" refers to any atom or group of atoms used to attach the lipophilic moiety to a myostatin siNA molecule. Linking groups or bifunctional linking moieties such as those known in the art are amenable to the present invention.

The terms "detecting" or "measuring," as used herein in connection with an activity, response or effect, indicate that a test for detecting or measuring such activity, response, or effect is performed. Such detection and/or measuring may include values of zero. Thus, if a test for detection or measuring results in a finding of no activity (activity of zero), the step of detecting or measuring the activity has nevertheless been performed.

The phrase "effective amount" as used herein refers to its meaning as is generally accepted in the art. The term generally refers to the amount of a molecule, compound or composition that will elicit the intended biological response of a cell, tissue, system, animal or human that is be sought by the researcher, veterinarian, medical doctor or other clinician (e.g., reduction in myostatin protein levels, as measured in muscle tissue or serum). A "therapeutically effective amount" generally refers to the amount of a molecule, compound or composition that will elicit the medical response if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The term "expression" as used herein refers to its meaning as is generally accepted in the art. The term generally refers to the process by which a gene ultimately results in a protein. Expression includes, but is not limited to, transcription, splicing, post-transcriptional modification and translation.

The term "gene" as used herein refers to its meaning as is generally accepted in the art. The term generally refers to a nucleic acid (e.g., DNA or RNA) sequence that comprises partial length or entire length coding sequences necessary for the production of a polypeptide. A gene can also include the UTR or non-coding region of the nucleic acid sequence. A gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Aberrant fRNA or ncRNA activity leading to disease can therefore be modulated by delivery of myostatin-directed siNA molecules by the methods of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The term "gene" can be used when referencing a gene to which an siNA molecule, delivered by the methods of present invention, is either directly (i.e., the siNA molecule comprises an antisense strand having partial or complete complementarity to the gene) or indirectly (i.e., the siNA molecule comprises an antisense strand having partial or complete complementarity to a gene in the expression or activity pathway of the gene) targeted.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. "Heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle," as used herein, is intended to mean a 3- to 10-membered aromatic or nonaromatic heterocycle containing from 1 to 4 heteroatoms selected from the group consisting of O, N and S, and includes bicyclic groups. "Heterocycle" includes the above mentioned heteroaryls, as well as dihydro and tetrahydro analogs thereof. Further examples of "heterocycle" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

The terms "including" (and any form thereof, such as "includes" and "include"), "comprising" (and any form thereof, such as "has" or "have") or "containing" (and any form thereof ("contains" or "contain") are inclusive and open-ended and do not exclude additional, unrecited elements or method steps.

The terms "inhibit," "down-regulate," or "reduce" as used herein refer to their meanings as generally accepted in the art. With reference to the siNA molecules delivered by the methods of the present invention, the term generally refers to reduction in the expression of a gene, or in the level of RNA molecules encoding one or more proteins or protein subunits, or in the activity of one or more proteins or protein subunits, below that observed in the absence of the siNA molecules. Down-regulation can be associated with post-transcriptional silencing, such as RNAi mediated cleavage.

The terms "intermittent" or "intermittently" as used herein refer to their meaning as generally accepted in the art. The terms generally refer to periodic stopping and starting at either regular or irregular intervals.

The terms "internucleoside linkage," "internucleoside linker," "internucleoside linking group," "internucleotide linkage," "internucleotide linker" or "internucleotide linking group" are used herein interchangeably and refer to any linker or linkage between two nucleoside (i.e., a heterocyclic base moiety and a sugar moiety) units, as is known in the art, including, for example, but not as limitation, phosphate, analogs of phosphate, phosphonate, guanidium, hydroxylamine, hydroxylhydrazinyl, amide, carbamate, alkyl, and substituted alkyl linkages. Internucleoside linkages constitute the backbone of a nucleic acid molecule. In one aspect, a nucleotide of an siNA molecule may be linked to a consecutive nucleotide through a linkage between the 3'-carbon of the sugar of the first nucleotide and the sugar moiety of the second nucleotide (herein referred to as a 3' internucleoside linkage). A 3'-5' internucleoside linkage, as used herein, refers to an internucleoside linkage that links two consecutive nucleoside units, wherein the linkage is between the 3' carbon of the sugar moiety of the first nucleoside and the 5' carbon of the sugar moiety of the second nucleoside. In another aspect, a nucleotide of an siNA molecule may be linked to a consecutive nucleotide through a linkage between the 2'-carbon of the sugar of the first nucleotide and the sugar moiety of the second nucleotide (herein referred to as a 2' internucleoside linkage). A 2'-5' internucleoside linkage, as used herein, refers to an internucleoside linkage that links two consecutive nucleoside units, wherein the linkage is between the 2' carbon of the sugar moiety of the first nucleoside and the 5' carbon of the sugar moiety of the second nucleoside.

The term "linker" or "spacer," as used herein, refers to their meaning as generally accepted in the art. Generally, they refer to any molecule that links or joins components. In the case of the present invention, a linker or spacer may be used to join a myostatin siNA molecule to a lipophilic molecule to form a myostatin siNA conjugate. The linker can be a nucleic acid or a non-nucleic acid-based linker. The term "biodegradable linker" refers to an optional linker molecule designed to connect the siNA molecule to the lipophilic moiety and which is susceptible to degradation in a biological system.

The term "livestock," in reference to animals, refers to domesticated animals, semi-domesticated animals or captive wild animals that are raised in an agricultural setting to produce commodities such as food, fiber and labor. Livestock animals include cattle, swine, fowl (e.g., chicken, turkey), sheep, bison, goats and the like.

The phrase "metered dose inhaler" or "MDI" refers to a unit comprising a can, a secured cap covering the can, and a formulation metering valve situated in the cap. MDI systems include a suitable channeling device. Suitable channeling devices comprise for example, a valve actuator and a cylindrical or cone-like passage through which medicament can be delivered from the filled canister via the metering valve to the nose or mouth of a patient such as a mouthpiece actuator.

The term "microRNA" or "miRNA" as used herein refers to its meaning as is generally accepted in the art. The term generally refers to a small non-coding RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research, 102, 3-9; He et al., 2004, Nat. Rev. Genet., 5, 522-531; Ying et al., 2004, Gene, 342, 25-28; and Sethupathy et al., 2006, RNA, 12:192-197). The phenomenon of RNA interference includes the endogenously induced gene silencing effects of miRNAs. As used herein, "microRNA mimetic" refers to an siNA molecule having a sequence that is at least partially identical to that of a microRNA. In certain embodiments, a microRNA mimetic comprises the microRNA seed region of a microRNA. In certain embodiments, a microRNA mimetic modulates translation of more than one target nucleic acid.

The term "modulate" or "modulation" as used herein refers to its meaning as is generally accepted in the art. With reference to nucleic acid molecules delivered by the methods of the present invention, the term refers to when the expression of a gene, or the level of one or more RNA molecules (coding or non-coding), or the activity of one or more RNA molecules or proteins or protein subunits, is up-regulated or down-regulated, such that expression level or activity is greater than or less than that observed in the absence of the molecule that effects modulation. For example, the term "modulate" in some embodiments can refer to inhibition and, in other embodiments, can refer to potentiation or up-regulation, e.g., of gene expression.

The phrases "muscle cell" or "muscle tissue" as used herein refers to their meaning as is generally accepted in the art. They refer to a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The phrase "myostatin siNA molecule" or "myostatin siNA" as used herein refers to a siNA molecule that targets a myostatin gene. The phrase "myostatin siNA conjugate" as used herein refers to a siNA molecule that targets a myostatin gene and is linked to a lipophilic moiety.

The phrase "non-base paired" refers to nucleotides that are not base paired between the sense strand or sense region and the antisense strand or antisense region of a double-stranded siNA molecule. Non-base paired nucleotides can include, for example, but not as limitation, mismatches, overhangs, and single stranded loops.

The term "non-nucleotide" refers to any group or compound that can be incorporated into a polynucleotide chain in the place of one or more nucleotide units, such as for example but not limitation, abasic moieties or alkyl chains. The group or compound is "abasic" in that it does not contain a commonly recognized nucleotide base, such as adenosine, guanine, cytosine, uracil or thymine and, therefore, lacks a nucleobase at the 1'-position.

The term "nucleobase" is used herein to refer to the heterocyclic base portion of a nucleotide. Nucleobases may be naturally occurring or may be modified. In certain embodiments, a nucleobase may comprise any atom or group of atoms capable of hydrogen bonding to a base of another nucleic acid.

The term "nucleotide" is used as is generally recognized in the art. Nucleotides generally comprise a heterocyclic base moiety (i.e., a nucleobase), a sugar, and an internucleoside linkage, e.g., a phosphate. The base can be a natural base (standard), a modified base, or a base analog, as are well known in the art. Such bases are generally located at the 1' position of a nucleotide sugar moiety. Additionally, the nucleotides can be unmodified or modified at the sugar, internucleoside linkage, and/or base moiety, (also referred to interchangeably as nucleotide analogs, modified nucleotides, non-natural nucleotides, non-standard nucleotides and others; see, for example, U.S. application Ser. No. 12/064,014 (published as US 20090176725)). A naturally occurring internucleoside linkage refers to a 3' to 5' phosphodiester linkage (also referred to herein as a 3'-5' phosphodiester linkage).

The term "overhang" as used herein refers to its meaning as is generally accepted in the art. With reference to exemplary double-stranded nucleic acid molecules delivered by the methods of the present invention, the term generally refers to the terminal portion of a nucleotide sequence that is not base-paired between the two strands of a double-stranded nucleic acid molecule. Overhangs, when present, are typically at the 3'-end of one or both strands in an siNA duplex.

The phrase "pharmaceutically acceptable carrier or diluent" as used herein refers to its meaning as it generally accepted in the art. The phrase generally refers to any substance suitable for use in administering to a subject, such as an animal. In certain embodiments, a pharmaceutically acceptable carrier or diluent is sterile saline. In certain embodiments, such sterile saline is pharmaceutical grade saline.

The term "phosphorothioate" refers to an internucleoside phosphate linkage comprising one or more sulfur atoms in place of an oxygen atom. Hence, the term phosphorothioate refers to both phosphorothioate and phosphorodithioate internucleoside linkages.

The term "ribonucleotide" as used herein refers to its meaning as is generally accepted in the art. The term generally refers to a nucleotide with a hydroxyl group at the 2' position of a β-D-ribofuranose moiety.

The term "RNA" as used herein refers to its generally accepted meaning in the art. Generally, the term RNA refers to a molecule comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of an siNA molecule or internally, for example at one or more nucleotides of the RNA. Nucleotides in the nucleic acid molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process generally known in the art of inhibiting or down regulating gene expression in a cell, typically by causing destruction of specific target RNA and mediated by sequence-specific nucleic acid molecules (e.g., short interfering nucleic acid molecule), see for example Zamore and Haley, 2005, *Science,* 309, 1519-1524; Vaughn and Martienssen, 2005, *Science,* 309, 1525-1526; Zamore et al., 2000, *Cell,* 101, 25-33; Bass, 2001, *Nature,* 411, 428-429; Elbashir et al., 2001, *Nature,* 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237; Hutvagner and Zamore, 2002, *Science,* 297, 2056-60; McManus et al., 2002, *RNA,* 8, 842-850; Reinhart et al., 2002, *Gene & Dev.,* 16, 1616-1626; and Reinhart & Bartel, 2002, *Science,* 297, 1831). Additionally, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at either the post-transcriptional level or the pre-transcriptional level. In a non-limiting example, epigenetic modulation of gene expression by siNA molecules delivered by the methods of the present invention can result from siNA mediated modification of chromatin structure or methylation patterns to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). Modulation of gene expression by siNA molecules delivered by the methods of the present invention can result from siNA mediated cleavage of RNA (either coding or non-coding RNA) via RISC.

The phrase "sense region" as used herein refers to its meaning as is generally accepted in the art. With reference to siNA molecules described herein, the term refers to a nucleotide sequence of an siNA molecule having complementarity to an antisense region of the siNA molecule. In addition, the sense region of a siNA molecule can comprise a nucleic acid sequence having homology or sequence identity with a target nucleic acid sequence. In one embodiment, the sense region of the siNA molecule is also referred to as the sense strand or passenger strand.

The phrases "short interfering nucleic acid," "siNA," "siNA molecule," "short interfering RNA," "siRNA," "short interfering nucleic acid molecule," "short interfering oligonucleotide molecule," or "chemically modified short interfering nucleic acid molecule" refer to any nucleic acid molecule capable of inhibiting or down regulating gene expression or viral replication by mediating RNA interference ("RNAi") in a sequence-specific manner. These terms can refer to both individual nucleic acid molecules, a plurality of such nucleic acid molecules, or pools of such nucleic acid molecules. The siNA can be a symmetric or asymmetric double-stranded nucleic acid molecule comprising self-complementary sense and antisense strands or regions, wherein the antisense strand/region comprises a nucleotide sequence that is complementary to a nucleotide sequence in a target nucleic acid molecule or a portion thereof, and the sense strand/region comprises a nucleotide sequence corresponding to the target nucleic acid sequence or a portion thereof. A symmetric duplex refers to an siNA molecule comprising sense and antisense regions each comprising the same number of nucleotides. An asymmetric duplex refers to an siNA molecule comprising an antisense region and a sense region that comprises fewer nucleotides than the antisense region, to the extent that the sense region has enough complementary nucleotides to base pair with the antisense region to form a duplex. For example, an asymmetric double-stranded siNA molecule can comprise an antisense region having length sufficient to mediate RNAi in a cell or in vitro system, e.g. about 15 to about 30, and a sense region having about 3 to about 25 nucleotides that are complementary to the antisense region. As an example, an asymmetric double-stranded hairpin siNA molecule can also comprise a loop region comprising about 4 to about 12 nucleotides. The loop portion of an asymmetric hairpin siNA molecule can comprise nucleotides, non-nucleotides, linker molecules, or conjugate molecules as described herein. An siNA molecule can also comprise a single-stranded polynucleotide having a nucleotide sequence complementary to a portion of a nucleotide sequence in a target nucleic acid molecule (for example, where such siNA molecule does not require the presence within the siNA molecule of a nucleotide sequence corresponding to the target nucleic acid sequence or a portion thereof). A single-stranded siNA molecule is an RNAi molecule, functioning through an RNAi mechanism.

The term "subject" as used herein refers to its meaning as is generally accepted in the art. As used herein, term generally refers to an organism to which the siNA conjugates as described and compositions thereof can be administered. The term "subject" is intended to include human and non-human animals. Non-human animals include all vertebrates, e.g. mammals and non-mammals, such as non-human primates, sheep, dogs, cats, cows, horses, chickens, amphibians, rabbits, hamsters, guinea pigs, livestock and reptiles. A subject can be an organism that has been previously identified as a suitable candidate for administration of the siNA conjugates as per the methods of the invention. For example, a subject can be a mammal, such as a human, diagnosed with a musculoskeletal disease, wherein it is believed that treatment with the siNA conjugates described herein has potential of resulting in a positive clinical outcome. The term "subject" is also intended to include an embryo, including a chicken embryo contained within an egg.

The term "sugar moiety" means a natural or modified sugar ring or sugar surrogate.

The term "sugar surrogate" generally refers to a structure that is capable of replacing the furanose ring of a naturally occurring nucleotide. In certain embodiments, sugar surrogates are non-furanose (or 4'-substituted furanose) rings or ring systems or open systems. Such structures include simple changes relative to the natural furanose ring, such as a 6-membered ring or may be more complicated as is the case with the non-ring system used in peptide nucleic acid. Sugar surrogates includes without limitation morpholinos, cyclohexenyls and cyclohexitols. In most nucleotides having a sugar surrogate group, the heterocyclic base moiety is generally maintained to permit hybridization.

The phrase "systemic administration" as used herein refers to its meaning as is generally accepted in the art. The term generally refers to methods or techniques of administering a molecule, drug, agent or compound in a manner resulting in in vivo systemic absorption or accumulation of drugs in the blood stream followed by distribution throughout the entire body. Systemic administration includes in ovo administration.

The term "target" cellular protein, peptide, or polypeptide, or polynucleotide or nucleic acid (such as "target DNA," "target RNA," "target nucleic acid"), as used herein, refers to a protein or nucleic acid, respectively, of which an siNA molecule may be capable of inhibiting or down regulating the expression. In certain embodiments, target RNA is mRNA, pre-mRNA, non-coding RNA, pri-micro-RNA, pre-microRNA, mature microRNA, promoter-directed RNA, or natural antisense transcripts. As used herein, "target mRNA" refers to a pre-selected RNA molecule that encodes a protein. As used herein, "target pre-mRNA" refers to a pre-selected RNA transcript that has not been fully processed into mRNA. Notably, pre-RNA includes one or more intron. As used herein, "target microRNA" refers to a pre-selected non-coding RNA molecule about 18-30 nucleobases in length that modulates expression of one or more proteins or to a precursor of such a non-coding molecule. As used herein, "target non-coding RNA" refers to a pre-selected RNA molecule that is not translated to generate a protein. Certain non-coding RNA is involved in regulation of expression.

The phrases "target site," "target sequence" and "target nucleic acid site" as used herein refer to their meanings as generally accepted in the art. The term generally refers to a sequence within a target nucleic acid (e.g., RNA) that is "targeted," e.g., for cleavage mediated by an siNA molecule that contains sequences within its antisense region that are complementary to the target sequence.

The phrase "universal base" as used herein refers to its meaning as is generally accepted in the art. The term universal base generally refers to nucleotide base analogs that form base pairs with each of the natural DNA/RNA bases with little or no discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001, *Nucleic Acids Research,* 29, 2437-2447).

The term "up-regulate" as used herein refers to its meaning as is generally accepted in the art. With reference nucleic acid molecules described herein, the term refers to an increase in either the expression of a gene, or the level of RNA molecules or equivalent RNA molecules encoding one or more proteins or protein subunits, or the activity of one or more RNAs, proteins or protein subunits, above that observed in the absence of the nucleic acid molecules (e.g., siNA) of the invention. In certain instances, up-regulation or promotion of gene expression with an siNA molecule is above that level observed in the presence of an inactive or attenuated molecule. In other instances, up-regulation or promotion of gene expression with siNA molecules is above that level observed in the presence of, for example, an siNA molecule with scrambled sequence or with mismatches. In still other instances, up-regulation or promotion of gene expression with a nucleic acid molecule of the instant invention is greater in the presence of the nucleic acid molecule than in its absence. In some instances, up-regulation or promotion of gene expression is associated with inhibition of RNA mediated gene silencing, such as RNAi mediated cleavage or silencing of a coding or non-coding RNA target that down-regulates, inhibits, or silences the expression of the gene of interest to be up-regulated. The down-regulation of gene expression can, for example, be induced by a coding RNA or its encoded protein, such as through negative feedback or antagonistic effects. The down-regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down-regulation of targets that down-regulate, suppress, or silence a gene of interest can be used to up-regulate expression of the gene of interest toward therapeutic use.

The term "vector" as used herein refers to its meaning as is generally accepted in the art. The term vector generally refers to any nucleic acid- and/or viral-based expression system or technique used to deliver one or more nucleic acid molecules.

B. Myostatin siNA Molecules

Myostatin is a known growth factor involved in regulation of muscle growth. In particular, myostatin is a member of the TGF-β family of growth factors and is a potent negative regulator of myogenesis. Knock-out mice for myostatin have greatly increased muscle mass over their entire body, having approximately 30% greater body weight than normal mice, and exhibiting a 2 to 3 fold increase in individual muscle weights due to muscle fiber hyperplasia and hypertrophy. Natural mutations in myostatin have been identified as being responsible for the "double-muscled" phenotype, such as the Belgian Blue and Piedmontese cattle breeds. See McPherron, A. C. et al, 1997, *Nature* 387:83-92; McPherron, A. C. et al., 1997, *Proc. Natl. Acad. Sci. USA* 94:12457-12461; Kambadur, R. et al., 1997, *Genome Res.* 7:910-916; Grobet, L. et al., 1997, *Nat. Genet.* 17:71-74).

The siNA molecules delivered by the methods of the present invention are designed to target a myostatin gene. The siNA molecules may be directed to a myostatin gene sequence derived from an array of suitable animals, including for example human, cattle, pigs, fowl or mouse. For example, a myostatin siNA molecule delivered by the methods of the present invention may be designed to target a myostatin mRNA as set forth in Table 1:

TABLE 1

| Species | NCBI GenBank Accession No. |
|---|---|
| Bos taurus | GQ184147 |
| Bos indicius | AY794986 |
| Home sapien | AF104922 |
| Sus scrofa | AY448008 |
| Equus caballus | AB033541 |
| Gallus gallus | AY448007 |
| Meleagris gallopavo | AF019625 |
| Ovis aries | AM992883 |
| Capra hircus | GQ246167 |
| Macaca fascicularis | AY055750 |
| Mus musculus | NM_010834 |

The instant invention features single- or double-stranded siNA molecules that target a myostatin gene, lipophilic conjugates thereof, and methods of delivering and using the same in vivo, wherein said delivered siNA molecules are capable of mediating RNA interference. The antisense strand (or guide strand) of the siNA portion of a myostatin siNA conjugate is complementary to a myostatin target nucleic acid. The siNA molecule portion of the conjugates can take different oligonucleotide forms, including but not limited to short interfering RNA (siRNA), double-stranded RNA (dsRNA), micro-RNA (miRNA) and short hairpin RNA (shRNA) molecules. In certain embodiments, the siNA molecule is single-stranded. In other embodiments, the siNA molecule is double-stranded molecules, wherein said double-stranded molecule comprises an antisense strand and a sense strand. The myostatin siNA molecules comprised within the myostatin siNA conjugates modulate expression of a myostatin target nucleic acid. In one embodiment, the siNA molecules inhibit or reduce expression of a myostatin target nucleic acid. In one aspect, the siNA molecule portion of the myostatin siNA conjugates is single-stranded, wherein the single oligonucleotide strand comprises a sequence that is complementary to at least a part of a myostatin nucleic acid associated with myostatin gene expression. For purposes of this disclosure, the single strand of a single-stranded siNA molecule is referred to as the antisense strand.

In another aspect, the siNA molecule portion of the myostatin siNA conjugates is a double-stranded siNA molecule, wherein a double-stranded siNA molecule comprises a sense and an antisense oligonucleotide strand. The antisense strand comprises a sequence that is complementary to at least a part of a myostatin target nucleic acid associated with myostatin gene expression, and the sense strand is complementary to the antisense strand. The double-stranded siNA molecules can comprise two distinct and separate strands that can be symmetric or asymmetric and are complementary, i.e., two single-stranded oligonucleotides, or can comprise one single-stranded oligonucleotide in which two complementary portions, e.g., a sense region and an antisense region (which, in this context, will be referred to herein as a sense strand and an antisense strand, respectively), are base-paired, and are covalently linked by one or more single-stranded "hairpin" areas (i.e. loops) resulting in, for example, a short-hairpin polynucleotide. The linker can be a polynucleotide linker or a non-nucleotide linker. In some embodiments, the linker is a non-nucleotide linker. In some embodiments, a hairpin siNA molecule contains one or more loop motifs, wherein at least one of the loop portions of the siNA molecule is biodegradable. For example, a short hairpin siNA molecule can be designed such that degradation of the loop portion of the siNA molecule in vivo can generate a double-stranded siNA molecule with 3'-terminal overhangs, such as 3'-terminal nucleotide overhangs comprising 1, 2, 3 or 4 nucleotides.

The antisense strand of the siNA molecule portion of the described conjugates is complementary to a portion of a myostatin target nucleic acid sequence. In some embodiments, the target nucleic acid is selected from a myostatin target mRNA, a myostatin target pre-mRNA, a myostatin target microRNA, and a myostatin target non-coding RNA. In certain embodiments, the antisense strand of the siNA molecule comprises a region that is 100% complementarity to a myostatin target nucleic acid sequence and wherein the region of 100% complementarity is at least 10 nucleobases. In certain embodiments, the region of 100% complementarity is at least 15 nucleobases. In certain embodiments, the region of 100% complementarity is at least 20 nucleobases.

In certain embodiments, the region of 100% complementarity is at least 25 nucleobases. In certain embodiments, the region of 100% complementarity is at least 30 nucleobases. In certain embodiments, the antisense strand of the siNA molecule is at least 85% complementary to a myostatin target nucleic acid sequence. In certain embodiments, the antisense strand is at least 90% complementary to a myostatin target nucleic acid sequence. In certain embodiments, the antisense strand is at least 95% complementary to a myostatin target nucleic acid sequence. In certain embodiments, the antisense strand is at least 98% complementary to a myostatin target nucleic acid sequence. In certain embodiments, the antisense strand is 100% complementary to a myostatin target nucleic acid sequence. The complementary nucleotides may or may not be contiguous nucleotides. In one embodiment, the complementary nucleotides are contiguous nucleotides.

In certain embodiments, the siNA molecule portion of the myostatin siNA conjugates that are administered in vivo as per the methods of the present invention have between about 15 to about 30 (e.g., about 15, 16, 17, 18, 19, 20, 21, 22, 23, 24, 25, 26, 27, 28, 29, or 30) nucleotides in the antisense strand that are complementary to a nucleotide sequence of a myostatin target nucleic acid. In certain embodiments, the siNA molecules of the invention comprise an antisense strand having at least 15 nucleotides having sequence complementarity to a myostatin target sequence. In certain embodiments, the siNA molecules of the invention comprise an antisense strand having at least 18 nucleotides having sequence complementarity to a myostatin target sequence. In certain embodiments, the siNA molecules of the invention comprise an antisense strand having at least 19 nucleotides having sequence complementarity to a myostatin target sequence. In certain embodiments, the siNA molecules of the invention comprise an antisense strand having at least 20 nucleotides having sequence complementarity to a myostatin target sequence. In certain embodiments, the siNA molecules of the invention comprise an antisense strand having at least 21 nucleotides having sequence complementarity to a myostatin target sequence. In certain embodiments of this aspect of the invention, the complementary nucleotides are contiguous nucleotides.

In some embodiments, a double-stranded siNA molecule comprised with the myostatin siNA conjugates described herein has perfect complementarity between the sense strand or sense region and the antisense strand or antisense region of the siNA molecule, with the exception of any overhanging region.

In yet other embodiments, a double-stranded siNA molecule has partial complementarity (i.e., less than 100% complementarity) between the sense strand or sense region and the antisense strand or antisense region of the siNA molecule. Thus, in some embodiments, the double-stranded nucleic acid molecules have between about 15 to about 30 (e.g., about 15, 16, 17, 18, 19, 20, 21, 22, 23, 24, 25, 26, 27, 28, 29, or 30) nucleotides in one strand (e.g., sense strand) that are complementary to the nucleotides of the other strand (e.g., antisense strand). In certain embodiments, the double-stranded siNA molecules have 17 nucleotides in the sense region that are complementary to nucleotides of the antisense region of the molecule. In certain embodiments, the double-stranded siNA molecules have 18 nucleotides in the sense region that are complementary to nucleotides of the antisense region of the molecule. In certain embodiments, the double-stranded siNA molecules have 19 nucleotides in the sense region that are complementary to nucleotides of the antisense region of the molecule. In certain embodiments, the double-stranded siNA molecules of the invention have 20 nucleotides in the sense region that are complementary to nucleotides of the antisense region of the molecule. In certain embodiments of this aspect of the invention, the complementary nucleotides between the strands are contiguous nucleotides.

For siNA molecules that are symmetric, each strand, the sense (passenger) strand and antisense (guide) strand, are independently about 15 to about 30 (e.g., about 15, 16, 17, 18, 19, 20, 21, 22, 23, 24, 25, 26, 27, 28, 29, or 30) nucleotides in length. Generally, each strand of a symmetric siNA molecule is about 19-24 (e.g., about 19, 20, 21, 22, 23 or 24) nucleotides in length. In certain embodiments, each strand of a symmetric siNA molecule is 19 nucleotides in length. In certain embodiments, each strand of a symmetric siNA molecule is 20 nucleotides in length. In certain embodiments, each strand of a symmetric siNA molecule is 21 nucleotides in length. In certain embodiments, each strand of a symmetric siNA molecule is 22 nucleotides in length.

For siNA molecules that are asymmetric, the antisense strand of the molecule is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length. Generally, the antisense strand of an asymmetric siNA molecule is about 19-24 (e.g., about 19, 20, 21, 22, 23 or 24) nucleotides in length. In one embodiment, the sense strand of an asymmetric siNA molecule is about 19-24 (e.g., about 19, 20, 21, 22, 23 or 24) nucleotides in length.

In yet other embodiments, siNA molecules comprised with the myostatin siNA conjugates described herein are hairpin siNA molecules, wherein the siNA molecules are about 25 to about 70 (e.g., about 25, 26, 27, 28, 29, 30, 31, 32, 33, 34, 35, 36, 40, 45, 50, 55, 60, 65, or 70) nucleotides in length.

In certain embodiments, siNA molecules comprised with the myostatin siNA conjugates described herein are microRNA mimetics, having a nucleotide sequence comprising a nucleotide portion that is fully or partially identical to a seed region of a myostatin-related microRNA. In certain embodiments, the nucleotide sequence of a microRNA mimetic has a nucleotide portion that is 100% identical to a seed region of a myostatin-related microRNA. In certain embodiments, the nucleotide sequence of a microRNA mimetic has a nucleotide portion that is at least 75% identical (e.g., about 75%, 80%, 85%, 90%, 95%, 96%, 97%, 98% or 99%) to a seed region of a myostatin-related microRNA. In certain embodiments, the nucleotide sequence of a myostatin-related microRNA mimetic has a nucleotide portion that is 75% identical to a seed region of a myostatin-related microRNA. In certain embodiments, the nucleotide sequence of a microRNA mimetic has a nucleotide portion that is 80% identical to a seed region of a myostatin-related microRNA. In certain embodiments, the nucleotide sequence of a microRNA mimetic has a nucleotide portion that is 90% identical to a seed region of a myostatin-related microRNA. In certain embodiments, the nucleotide sequence of a microRNA mimetic has a nucleotide portion that is 95% identical to a seed region of a myostatin-related microRNA.

In other embodiments, siNA molecules comprised within the myostatin siNA conjugates described herein can contain one or more nucleotide deletions, substitutions, mismatches and/or additions (in reference to a myostatin target site sequence, or between strands of a duplex siNA molecule); provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair. Thus, in some embodiments, for example, double-stranded nucleic acid siNA molecules have one or more (e.g., 1, 2, 3, 4, 5, or 6) nucleotides in one strand or region (e.g., sense strand) that are mismatches or non-base-paired with the other strand or region (e.g., antisense strand). In certain embodiments, the siNA molecules contain no more than 3 mismatches. If the antisense strand of an siNA molecule contains mismatches to a myostatin target sequence, it is preferable that the area of mismatch is not located in the center of a contiguous region of complementarity.

In certain embodiments, the siNA molecules comprised with the conjugates described herein comprise overhangs of about 1 to about 4 (e.g., about 1, 2, 3 or 4) nucleotides. The nucleotides in the overhangs can be the same or different nucleotides. In some embodiments, the overhangs occur at the 3'-end (or the 3' terminus) of one or both strands of double-stranded siNA molecules. For example, a double-stranded siNA molecule can comprise a nucleotide or non-nucleotide overhang at the 3'-end of the antisense strand/region, at the 3'-end of the sense strand/region, or at the 3' ends of both the antisense strand/region and the sense strand/region. Overhanging nucleotides can be modified or unmodified.

In some embodiments, the nucleotides comprising the overhanging portion of an siNA molecule comprise sequences based on a myostatin target nucleic acid sequence in which the nucleotides comprising the overhanging portion of the antisense strand/region are complementary to nucleotides in the myostatin target polynucleotide sequence and/or the nucleotides comprising the overhanging portion of the sense strand/region comprise nucleotides from the myostatin target polynucleotide sequence. Thus, in some embodiments, the overhang comprises a two nucleotide overhang that is complementary to a portion of the myostatin target polynucleotide sequence. In other embodiments, however, the overhang comprises a two nucleotide overhang that is not complementary to a portion of the myostatin target nucleic acid sequence. In certain embodiments, the overhang comprises a 3'-UU overhang that is not complementary to a portion of the myostatin target nucleic acid sequence. In other embodiments, the overhang comprises a UU overhang at the 3' end of the antisense strand and a TT overhang at the 3' end of the sense strand.

In any of the embodiments of the siNA molecules described herein having 3'-end nucleotide overhangs, the overhangs are optionally chemically-modified at one or more nucleic acid sugar, base, or backbone positions. Representative, but not limiting examples of modified nucleotides in the overhanging portion of a double-stranded siNA molecule include the following: 2'-O-alkyl (e.g., 2'-O-methyl), 2'-deoxy, 2'-deoxy-2'-fluoro, 2'-deoxy-2'-fluoroarabino (FANA), 4'-thio, 2'-O-trifluoromethyl, 2'-O-ethyl-trifluoromethoxy, 2'-O-difluoromethoxy-ethoxy, universal base, acyclic, or 5-C-methyl nucleotides. In more preferred embodiments, the overhang nucleotides are each independently, a 2'-O-alkyl nucleotide, a 2'-O-methyl nucleotide, a 2'-deoxy-2-fluoro nucleotide, or a 2'-deoxy ribonucleotide. In some instances the overhanging nucleotides are linked by one or more phosphorothioate linkages.

In yet other embodiments, siNA molecules comprised within the myostatin siNA conjugates described herein comprise duplex nucleic acid molecules with blunt ends (i.e., without nucleotide overhangs), where both termini of the molecule are blunt, or alternatively, where one of the ends is blunt. In some embodiments, the siNA molecules comprise one blunt end, for example wherein the 5'-end of the antisense strand and the 3'-end of the sense strand do not have any overhanging nucleotides, or wherein the 3'-end of the antisense strand and the 5'-end of the sense strand do not have any overhanging nucleotides. In other embodiments, siNA molecules comprise two blunt ends, for example wherein the 3'-end of the antisense strand and the 5'-end of the sense strand, as well as the 5'-end of the antisense strand and 3'-end of the sense strand, do not have any overhanging nucleotides.

In any of the embodiments or aspects of the siNA molecules comprised within the myostatin siNA conjugates described herein, the sense strand and/or the antisense strand can further have a cap, such as described herein or as known in the art. A cap can be present at the 3'-end of the antisense strand, the 5'-end of the sense strand, and/or the 3'-end of the sense strand. In the case of a hairpin siNA molecule, a cap can be present at the 3'-end of the polynucleotide. In some embodiments, a cap is at one or both ends of the sense strand of a double-stranded siNA molecule. In other embodiments, a cap is at the 3'-end of antisense (guide) strand. In other embodiments, a cap is at the 3'-end of the sense strand and at the 5'-end of the sense strand. Representative but non-limiting examples of such terminal caps include an inverted abasic nucleotide and derivatives thereof, an inverted nucleotide moiety, a glyceryl modification, an alkyl or cycloalkyl group, a heterocycle or any other cap as is generally known in the art.

Any of the embodiments of the siNA molecules described herein can have a 5' phosphate terminus. In some embodiments, the siNA molecules lack terminal phosphates.

In certain embodiments, double-stranded siNA molecules comprised within the myostatin siNA conjugates described herein comprise about 3 to about 30 (e.g., about 3, 4, 5, 6, 7, 8, 9, 10, 11, 12, 13, 14, 15, 16, 17, 18, 19, 20, 21, 22, 23, 24, 25, 26, 27, 28, 29, or 30) base pairs. Generally, the duplex structure of siNA molecules is between 15 and 30 base pairs, more generally between 18 and 25 base pairs, yet more generally between 19 and 24 base pairs, and most generally between 19 and 21 base pairs in length. In one embodiment, a double-stranded siNA molecule comprises 19 base pairs. In one embodiment, a double-stranded siNA molecule comprises 20 base pairs. In one embodiment, a double-stranded siNA molecule comprises 21 base pairs. The double-stranded siNA molecules can be asymmetric or symmetric. In other embodiments of this aspect of the invention, the siNA duplex molecules are hairpin structures.

Any siNA molecule can comprise one or more chemically-modified nucleotides. Modifications can be used to improve in vitro or in vivo characteristics such as stability, activity, toxicity, immune response (e.g., prevent stimulation of an interferon response, an inflammatory or pro-inflammatory cytokine response, or a Toll-like Receptor response), and/or bioavailability. Various chemically modified siNA motifs disclosed herein have the potential to maintain an RNAi activity that is substantially similar to either unmodified or minimally-modified active siRNA (see for example Elbashir et al., 2001, *EMBO J.*, 20:6877-6888) while, at the same time, providing nuclease resistance and pharmacokinetic properties suitable for use in therapeutic applications.

In certain embodiments of the siNA molecules comprised with the myostatin siNA conjugates used by the methods of the present invention, any (e.g., one, more or all) nucleotides present in the antisense and/or sense strand may be modified nucleotides (e.g., wherein one nucleotide is modified, some nucleotides (i.e., a plurality or more than one) are modified, or all nucleotides of the molecule are modified nucleotides). Modifications include sugar modifications, base modifications, backbone (internucleoside linkage) modifications, non-nucleotide modifications, and/or any combination thereof.

Non-limiting examples of chemical modifications that are suitable for use in the siNA molecule portion of the conjugates described herein are disclosed in U.S. Pat. No. 8,202,979 and U.S. patent application Ser. Nos. 10/981,966 and 12/064,014 (published as US 20050266422 and US 20090176725, respectively), and in references cited therein, and include sugar, base, and backbone modifications, non-nucleotide modifications, and/or any combination thereof. These U.S. patents and applications are incorporated hereby as references for the purpose of describing chemical modifications that are suitable for use with the siNA molecules.

The chemical modifications of nucleotides present within a single siNA molecule can be the same or different. In some embodiments, at least one strand of an siNA molecule has at least one chemical modification. In other embodiments, each strand has at least one chemical modification, which can be the same or different, such as sugar, base, or backbone (i.e., internucleotide linkage) modifications. In other embodiments, siNA molecules contain at least 2, 3, 4, 5, or more different chemical modifications.

In some embodiments, the siNA molecules comprised within the myostatin siNA conjugates administered as per the methods of the present invention are partially modified (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, or 59 nucleotides are modified) with chemical modifications. In some embodiments, an siNA molecule comprises at least about 8, 10, 12, 14, 16, 18, 20, 22, 24, 26, 28, 30, 32, 34, 36, 38, 40, 42, 44, 46, 48, 50, 52, 54, 56, 58, or 60 nucleotides that are modified nucleotides, excluding the 5' modified nucleotide of the antisense strand. In other embodiments, the siNA molecules are completely modified (100% modified) with chemical modifications, i.e., the siNA molecule does not contain any ribonucleotides. In some embodiments, one or more of the nucleotides in the sense strand of the siNA molecules are modified. In the same or other embodiments, one or more of the nucleotides in the antisense strand of the siNA molecules are modified, excluding the 5' modified nucleotide of the antisense strand. In some embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of the nucleotide positions independently in either one or both strands of an siNA molecule are modified.

Modified nucleotides contained within the siNA molecules include those with modifications at the 2'-carbon of a sugar moiety and/or the 3'-carbon of a sugar moiety of a nucleotide. In certain specific embodiments of the invention, at least one modified nucleotide is a 2'-deoxy-2-fluoro nucleotide, a 2'-deoxy nucleotide, a 2'-O-alkyl (e.g., 2'-O-methyl) nucleotide, a 2'-methoxyethoxy or a locked nucleic acid (LNA) nucleotide, as is generally recognized in the art.

In yet other embodiment of the invention, at least one nucleotide has a ribo-like, Northern or A form helix configuration (see e.g., Saenger, Principles of Nucleic Acid Structure, Springer-Verlag ed., 1984). Non-limiting examples of nucleotides having a Northern configuration include locked nucleic acid (LNA) nucleotides (e.g., 2'-0,4'-C-methylene-(D-ribofuranosyl) nucleotides); 2'-methoxyethoxy (MOE) nucleotides; 2'-methyl-thio-ethyl nucleotides; 2'-deoxy-2'-fluoro nucleotides; 2'-deoxy-2'-chloro nucleotides; 2'-azido nucleotides; 2'-O-trifluoromethyl nucleotides; 2'-O-ethyl-trifluoromethoxy nucleotides; 2'-O-difluoromethoxy-ethoxy nucleotides; 4'-thio nucleotides; and 2'-O-methyl nucleotides. In various embodiments, a majority (e.g., greater than 50%) of the pyrimidine nucleotides present in a double-stranded siNA molecule comprises a sugar modification. In some of the same and/or other embodiments, a majority (e.g., greater than 50%) of the purine nucleotides present in a double-stranded siNA molecule comprises a sugar modification.

In certain instances, purine and pyrimidine nucleotides of an siNA molecule are differentially modified. In one example, purine and pyrimidine nucleotides can be differentially modified at the 2'-carbon of the sugar moiety (i.e., at least one purine has a different modification from at least one pyrimidine in the same or different strand at the 2'-carbon of the sugar moiety). In certain embodiments, the purines are unmodified in one or both strands, while the pyrimidines in one or both strands are modified. In certain other instances, the pyrimidines are unmodified in one or both strands, while the purines in one or both strands are modified. In certain instances, wherein the siNA molecules comprise one or more modifications as described herein, the nucleotides at positions 2 and 3 at the 5' end of the antisense (guide) strand are unmodified.

In some embodiments of the siNA molecules, the pyrimidine nucleotides in the antisense strand are 2'-O-methyl or 2'-deoxy-2'-fluoro pyrimidine nucleotides, and the purine nucleotides present in the antisense strand are 2'-O-methyl nucleotides or 2'-deoxy nucleotides. In certain embodiments, all of the pyrimidine nucleotides in a complementary region of an antisense strand of an siNA molecule are 2'-deoxy-2'-fluoro pyrimidine nucleotides. In certain embodiments, all of the purines in the complementary region on the antisense strand are 2'-O-methyl purine nucleotides.

In other embodiments of the siNA molecules, the pyrimidine nucleotides in the sense strand are 2'-deoxy-2'-fluoro pyrimidine nucleotides, and the purine nucleotides present in the sense strand are 2'-O-methyl or 2'-deoxy purine nucleotides. In certain embodiments of the invention, all the pyrimidine nucleotides in the complementary region on the sense strand are 2'-deoxy-2'-fluoro pyrimidine nucleotides. In certain embodiments, all the purine nucleotides in the complementary region on the sense strand are 2'-deoxy purine nucleotides.

In certain embodiments, all of the pyrimidine nucleotides in the complementary regions on the sense strand are 2'-deoxy-2'-fluoro pyrimidine nucleotides; all of the pyrimidine nucleotides in the complementary region of the antisense strand are 2'-deoxy-2'-fluoro pyrimidine nucleotides; all the purine nucleotides in the complementary region on the sense strand are 2'-deoxy purine nucleotides and all of the purines in the complementary region on the antisense strand are 2'-O-methyl purine nucleotides.

In some embodiments, at least 5 or more of the pyrimidine nucleotides in one or both strands of an siNA molecule are 2'-deoxy-2'-fluoro pyrimidine nucleotides. In some embodiments, at least 5 or more of the pyrimidine nucleotides in one or both strands are 2'-O-methyl pyrimidine nucleotides. In some embodiments, at least 5 or more of the purine nucleotides in one or both strands are 2'-deoxy-2'-fluoro purine nucleotides. In some embodiments, at least 5 or more of the purine nucleotides in one or both strands are 2'-O-methyl purine nucleotides.

In certain embodiments, the siNA molecules comprise one or more modified internucleoside linking group. A modified internucleoside linking group is a linking group other than a phosphodiester 3'-5' internucleoside linking group, including but not limited to 2' internucleoside linking groups (e.g., phosphodiester and phosphorothioate 2'-5' internucleoside linkages). In certain embodiments, each internucleoside linking group is, independently, a 2' or 3' phosphodiester or phosphorothioate internucleoside linking group. In certain embodiments, the 5'-most internucleoside linking group on either or both strands of an siNA molecule is a phosphorothioate linking group. In certain embodiments, the siNA molecules comprise from 3 to 12 contiguous phosphorothioate linking groups, wherein the phosphorothioate linking groups are either 2' or 3' internucleoside linking groups. In certain embodiments, the siNA molecules comprise from 6 to 8 contiguous phosphorothioate linking groups, wherein the phosphorothioate linking groups are either 2' or 3' internucleoside linking groups. In certain embodiments, the 3' end of the antisense and/or sense strand of the siNA molecules comprises a phosphorothioate linking groups. In certain embodiments, the siNA molecules comprise from 6 to 8 contiguous phosphorothioate linking groups at the 3' end of the antisense and/or sense strand, wherein the phosphorothioate linking groups are either 2' or 3' internucleoside linking groups.

Any of the above described modifications, or combinations thereof, including those in the references cited, can be applied to any of the siNA molecules comprised within the myostatin siNA conjugates that are administered as per the methods and uses of the present invention.

The myostatin siNA molecules can be obtained using a number of techniques known to those of skill in the art. For example the siNA molecules can be chemically synthesized using protocols known in the art (for example, as described in: Caruthers et al., 1992, Methods in Enzymology 211, 3-19; Thompson et al., International PCT Publication No. WO 99/54459; Wincott et al., 1995, Nucleic Acids Res. 23, 2677-2684; Wincott et al., 1997, Methods Mol. Bio., 74, 59; Brennan et al., 1998, Biotechnol Bioeng., 61, 33-45; Brennan, U.S. Pat. No. 6,001,311; Usman et al., 1987, J. Am. Chem. Soc., 109, 7845; and Scaringe et al., 1990, Nucleic Acids Res., 18, 5433). The syntheses of oligonucleotides described in the art makes use of common nucleic acid protecting and coupling groups, such as dimethoxytrityl at the 5'-end and phosphoramidites at the 3'- or 2'-end.

In certain embodiments, the siNA molecules are synthesized, deprotected, and analyzed according to methods described in, for example, U.S. Pat. Nos. 6,995,259, 6,686,463, 6,673,918, 6,649,751, 6,989,442, and 7,205,399. In a non-limiting synthesis example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides.

Alternatively, the siNA molecules can be synthesized separately and joined together post-synthetically, for example, by ligation (e.g., Moore et al., 1992, Science 256, 9923; Draper et al., International PCT Publication No. WO 93/23569; Shabarova et al., 1991, Nucleic Acids Research 19, 4247; Bellon et al., 1997, Nucleosides & Nucleotides, 16, 951; and Bellon et al., 1997, Bioconjugate Chem. 8, 204), or by hybridization following synthesis and/or deprotection.

C. Myostatin siNA Conjugates

The present invention provides myostatin siNA molecules capable of mediating RNA interference and reducing the in vivo expression of myostatin and methods for delivering the same to a subject, wherein the siNA molecules that are delivered as per the methods disclosed herein are linked to a lipophilic moiety, such as cholesterol. The lipophilic moiety-linked myostatin siNA molecules are referred to herein as myostatin siNA conjugates. In one embodiment, the myostatin siNA conjugates delivered by the methods of the present invention are not formulated within lipid formulations that form liposomes (e.g., a lipid nanoparticle). While not wishing to be bound by any particular theory, it is believed the attachment of a lipophilic moiety increases the lipophilicity of the myostatin siNA molecule, enhancing the entry of the siNA molecule into muscle cells.

Examples of lipophilic moieties that can be linked to a myostatin siNA molecule to form a myostatin siNA conjugate include, but are not limited to cholesterol, oleic acid, stearic acid, palmitic acid, myristic acid, linoleic acid, oleyl, retinyl, cholesteryl residues, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, O3-(oleoyl)lithocholic acid, O3-(oleoyl)cholenic acid, dimethoxytrityl, or phenoxazine. In a preferred embodiment, the linked lipophilic moiety is cholesterol.

In certain embodiments, the lipophilic moiety is attached directly to the siNA molecule. In these embodiments, the lipophilic moiety is still considered, for the purposes of the present invention, to be "linked" or "conjugated" to the siNA molecule. In certain embodiments, the lipophilic moiety is attached to the siNA molecule by means of a conventional linker or spacer molecule. The linker or spacer can be a nucleic acid or non-nucleic acid linker/spacer. A number of linker molecules are commercially available. Suitable linkers include, but are not limited to, straight or branched-chain carbon linkers, heterocyclic carbon linkers, or peptide linkers. Although a linker or spacer molecule generally has no specific biological activity other than to join the molecules being combined, or to preserve some minimum distance or other spatial relationship between them, the constituent amino acids of a peptide spacer may be selected to influence some property of the molecule such as the folding, net charge, or hydrophobicity.

The linker/spacer can be a nucleic acid linker that is biodegradable. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. A biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidite or phosphodiester linkage. A biodegradable nucleic acid linker molecule can also comprise nucleic acid backbone, nucleic acid sugar, or nucleic acid base modifications.

The lipophilic moiety is attached to a myostatin siNA molecule through attachment to either a terminus of the siNA molecule (e.g., the 3' or 5' end of an oligonucleotide strand of the siNA molecule) or through linkage to an internal nucleotide of the siNA molecule. In one embodiment, the lipophilic moiety is attached to the 3' end of the passenger strand (sense strand) of a double-stranded myostatin siNA molecule. In one embodiment, the lipophilic moiety is attached to the 5' end of the passenger strand of a double-stranded myostatin siNA molecule. In a further embodiment, the lipophilic moiety is attached to the 3' end of the guide strand (antisense strand) of a myostatin siNA molecule. In a further embodiment, the lipophilic moiety is attached to the 5' end of the guide strand (antisense strand) of a myostatin siNA molecule. In a further embodiment, a myostatin siNA conjugate contains more than one attached lipophilic moiety (e.g., a lipophilic moiety attached to both the 3' and the 5' end of the passenger strand; a lipophilic moiety attached to the 3' end of the guide strand and the 5' end of the passenger strand). In this aspect of the invention, the lipophilic moieties can be the same or different.

In certain embodiments, a myostatin siNA conjugate is prepared by chemically conjugating all or a portion of a myostatin siNA molecule to the lipophilic group. Means of chemically conjugating molecules are well known to those of skill in the art. Such means will vary according to the structure of the moiety to be attached, but will be readily ascertainable to those of skill in the art.

The present invention further provides myostatin siNA conjugates in kit form. The kit may comprise a container. In one embodiment, the kit contains one or more myostatin siNA conjugate with instructions for systemic administration. The kits may comprise a myostatin siNA conjugate within a pharmaceutically acceptable carrier or diluent. The kits may further comprise excipients.

D. Uses

The methods for systemically administering myostatin siNA conjugates described herein are useful to modulate and or regulate (e.g., inhibit, down-regulate) the in vivo expression and/or activity of a myostatin target nucleic acid (e.g., a myostatin target gene) by an RNAi interference mechanism (e.g., by degrading a myostatin mRNA). Modulation of the in vivo expression of a myostatin target nucleic acid results increased muscle mass and/or enhanced muscle performance. The methods may be further useful in therapeutic regimens to treat one or more musculoskeletal disease states. In one embodiment, inhibition of a disease may be evaluated by directly measuring the progress of the disease in a subject. It may also be inferred through observing a change or reversal in a condition associated with the disease. The methods of the present invention have the further potential of being used as a prophylaxis. Thus, use of the myostatin siNA conjugates and pharmaceutical compositions described herein have the potential of ameliorating, treating, preventing, and/or curing diseases states associated with regulation of myostatin gene expression. The myostatin siNA conjugates further have the potential for use in cosmetic applications and/or for veterinary purposes to increase muscle mass and/or enhance muscle performance.

In an embodiment of the invention, the subject to which a myostatin siNA conjugate described herein is systemically administered is suffering from a musculoskeletal disease or disorder. In one embodiment, a musculoskeletal disease or disorder includes a condition that causes or results in muscle atrophy. Muscle atrophy can result from treatment with a glucocorticoid such as cortisol, dexamethasone, betamethasone, prednisone, methylprednisolone or prednisolone. Muscle atrophy can also be a result of denervation due to nerve trauma or a result of degenerative, metabolic or inflammatory neuropathy. For example, muscle atrophy can be a result of an adult motor neuron disease, Guillian-Barré syndrome, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, and metabolic stress or nutritional insufficiency. Muscle atrophy can be a result of myopathy, including for example myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositis; polymyositis; inclusion body myositis; myositis ossificans; rhabdomyolysis and myoglobinurias. Myopathy may be caused by a muscular dystrophy syndrome, such as Duchenne muscular dystrophy (DMD), Becker muscular dystrophy (also known as benign pseudohypertrophic muscular dystrophy), myotonic dystrophy, scapulohumeral and fascioscapulohumeral muscular dystrophy, Emery-Dreifuss muscular dystrophy, oculopharyngeal muscular dystrophy, limb girdle muscular dystrophy, Fukuyama congenital muscular dystrophy, or hereditary distal myopathy.

Further examples musculoskeletal disease or disorder or conditions that result in musculoskeletal disease or disorder include sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, cancer, stroke, frailty, memory loss, impaired kidney function, metabolic disorders (including Type-II diabetes, metabolic syndrome, hyperglycemia, obesity, thyroid gland disorder), cachexia (including cachexia associated with a rheumatoid arthritis and cachexia associated with cancer), acute and/or chronic renal disease or failure, liver diseases (examples such as fibrosis, cirrhosis), cancer (including rhabdomyosarcoma, prostate cancer, breast cancer, hepatocellular carcinoma, and gastrointestinal cancer), Parkinson's Disease; anemia, exposure to environmental toxins or drugs, HIV/AIDS, fasting, benign congenital hypotonia, central core disease, burn injury, chronic obstructive pulmonary disease, sepsis, congestive heart failure, aging or an age-related condition, and space travel or time spent in a zero gravity environment.

The myostatin siNA conjugates and pharmaceutical formulations thereof can be administered to a subject alone or used in combination with one or more other therapies, including known therapeutic agents, treatments, or procedures to prevent or treat musculoskeletal diseases, disorders, conditions, and traits. A combination can conveniently be presented for use in the form of a pharmaceutical composition, wherein the pharmaceutical composition comprises a combination that includes a myostatin siNA conjugate, a pharmaceutically acceptable diluent or carrier, and one or more additional therapeutic agents. Alternatively, the individual components of such combinations can be administered either sequentially or simultaneously in separate or combined pharmaceutical formulations.

Combinations of the methods of the invention with standard medical treatments (e.g., corticosteroids for muscular dystrophies) are specifically contemplated, as are combinations with novel therapies. For example, for treatment of genetic muscular dystrophies, methods of the invention may be combined with follistatin administration, followed by simultaneous or concomitant treatment to correct the genetic disorder. Correcting a genetic disorder may involve, for example, replacing sarcoglycans in sarcoglycan deficiency, correcting or replacing dystrophin in disorders such as Duchenne's Muscular Dystrophy, treating ALS patients with IGF-1 or mutant SOD1 interference strategies. Given that in a disorder contemplated for treatment by the methods of the present invention, a significant amount of muscle may be lost, the rescue of muscle will provide a substrate (preserved or regenerated muscle) for subsequent gene correction. In this respect, it may be conceivable to inhibit myostatin to enhance muscle, increase muscle size, and then provide the secondary treatment. Such secondary treatments for muscular dystrophy may be IGF-1, exon-skipping, calpain inhibition, dystrophin upregulation, and dystroglycan expression. Myostatin inhibition in concert with muscle precursor cells (satellite cells, stem cells) may allow more of these cells to be incorporated into the tissue.

E. Pharmaceutical Compositions

The myostatin siNA conjugates of the invention are preferably formulated as pharmaceutical compositions prior to systemically administering to a subject, according to techniques known in the art. Pharmaceutical compositions are characterized as being at least sterile and pyrogen-free. Methods for preparing pharmaceutical compositions are within the skill in the art for example as described in *Remington's Pharmaceutical Science*, $17^{th}$ ed., Mack Publishing Company, Easton, Pa. (1985).

Pharmaceutical compositions of the myostatin siNA conjugates further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, e.g., DTPA or DTPA-bisamide) or calcium chelate complexes (e.g. calcium DTPA, CaNaDTPA-bisamide), or, optionally, additions of calcium or sodium salts (e.g., calcium chloride, calcium ascorbate, calcium gluconate or calcium lactate). In addition, antioxidants and suspending agents can be used.

Compositions intended for oral use may be prepared according to methods known in the art for the manufacture of pharmaceutical compositions, especially methods known in the art for the manufacture of pharmaceutical compositions comprising oligonucleotides. For example, oral delivery of siRNA and antisense oligonucleotides has been achieved through encapsulating siRNA within biodegradable particles that protect them from degradation and target them to M cells in intestinal Peyer's patches (see Akhtar, S., 2009, *J. Drug Target.* 17:491-495). Oral composition can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, e.g., inert diluents (such as calcium carbonate, sodium carbonate, lactose, calcium phosphate or sodium phosphate), granulating and disintegrating agents (e.g., corn starch, or alginic acid), binding agents (e.g., starch, gelatin or acacia), and lubricating agents (e.g., magnesium stearate, stearic acid or talc). The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use may also be presented as hard gelatin capsules wherein the active ingredient is mixed with an inert solid diluent, e.g., calcium carbonate, calcium phosphate or kaolin, or as soft gelatin capsules wherein the active ingredient is mixed with water or an oil medium, e.g., peanut oil, liquid paraffin or olive oil.

Aqueous suspensions contain the active materials in a mixture with excipients suitable for the manufacture of aqueous suspensions. Such excipients are suspending agents, e.g., sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, e.g., lecithin, or condensation products of an alkylene oxide with fatty acids, e.g., polyoxyethylene stearate; or condensation products of ethylene oxide with long chain aliphatic alcohols, e.g., heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, e.g., polyethylene sorbitan monooleate. The aqueous suspensions can also contain one or more preservatives, e.g. ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, e.g. arachis oil, olive oil, sesame oil or coconut oil, or in a mineral oil such as liquid paraffin. The oily suspensions can contain a thickening agent, e.g. beeswax, hard paraffin or cetyl alcohol. Sweetening agents and flavoring agents can be added to provide palatable oral preparations. These compositions can be preserved by the addition of an anti-oxidant such as ascorbic acid Pharmaceutical compositions of the invention can also be in the form of oil-in-water emulsions. The oily phase can be a vegetable oil or a mineral oil or mixtures of these. Suitable emulsifying agents can be naturally-occurring gums, e.g. gum acacia or gum tragacanth, naturally-occurring phosphatides, e.g. soy bean, lecithin, and esters or partial esters derived from fatty acids and hexitol, anhydrides, for example sorbitan monooleate, and condensation products of the said partial esters with ethylene oxide, e.g. polyoxyethylene sorbitan monooleate. The emulsions can also contain sweetening and flavoring agents.

Syrups and elixirs can be formulated with sweetening agents, e.g. glycerol, propylene glycol, sorbitol, glucose or sucrose. Such formulations can also contain a demulcent, a preservative, and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The myostatin siNA conjugates can take the form of suppositories, e.g., for rectal administration of the drug.

These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Myostatin siNA conjugates described herein can be formulated in a sterile medium for intravenous administration. The molecule, depending on the vehicle and concentration used, can either be suspended or dissolved in the vehicle. Advantageously, adjuvants such as local anesthetics, preservatives and buffering agents can be dissolved in the vehicle.

In other embodiments, myostatin siNA conjugate formulations provided herein for use in pulmonary delivery further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, and/or choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

In one embodiment, myostatin siNA conjugates can be formulated for administration via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the siNA conjugate compositions can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Spray compositions comprising siNA conjugates described herein can, for example, be formulated as aqueous solutions or suspensions or as aerosols delivered from pressurized packs, such as a metered dose inhaler, with the use of a suitable liquefied propellant. In one embodiment, aerosol compositions suitable for inhalation can be either a suspension or a solution and generally contain an siNA conjugate and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition can optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment, a pharmaceutical aerosol formulation comprises an siNA conjugate and a fluorocarbon or hydrogen-containing chlorofluorocarbon or mixtures thereof as propellant, optionally in combination with a surfactant and/or a co-solvent.

The aerosol formulations can be buffered by the addition of suitable buffering agents.

Aerosol formulations can include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions. In another embodiment, a device comprising a nebulizer delivers an siNA conjugate composition comprising fluorochemicals that are bacteriostatic thereby decreasing the potential for microbial growth in compatible devices.

Capsules and cartridges comprising the myostatin siNA conjugate compositions for use in an inhaler or insufflator, of for example gelatin, can be formulated containing a powder mix for inhalation of a compound of the invention and a suitable powder base such as lactose or starch. In one embodiment, each capsule or cartridge contains an siNA conjugate and one or more excipients. In another embodiment, an siNA conjugate can be presented without excipients such as lactose.

The siNA conjugates can also be formulated as a fluid formulation for delivery from a fluid dispenser, such as those described and illustrated in WO05/044354.

F. Administration

The myostatin siNA conjugates and pharmaceutical compositions thereof are introduced into a subject by any of a variety of forms of systemic administration. For the purposes of the present invention, systemic administration include pulmonary (inhalation, nebulization etc.), intravenous, subcutaneous, catheterization, nasopharyngeal, or oral/gastrointestinal administration as is generally known in the art. Further non-limiting examples of administration methods of the invention include buccal, sublingual, parenteral (i.e., intravenously, intraperitoneally, subcutaneously, or intramuscularly), local rectal administration or other local administration resulting in absorption or accumulation of the myostatin siNA conjugates in the blood stream followed by distribution throughout the entire body. In one embodiment, the myostatin siNA conjugates and pharmaceutical compositions thereof can be administered by insufflation and inhalation. In one embodiment, the myostatin siNA conjugates and pharmaceutical compositions thereof are administered intravenously or intraperitoneally by a bolus injection (see, e.g., U.S. Pat. No. 5,286,634). In another embodiment, the myostatin siNA conjugates and pharmaceutical compositions thereof are administered subcutaneously. In a further embodiment, the myostatin siNA conjugates and pharmaceutical compositions thereof are administered in ovo to an avian embryo while contained in the egg. The siNA conjugates may be administered to any suitable compartment of the egg (e.g., allantois fluid, yolk sac, amnion, air cell or into the embryo).

For therapeutic applications, a pharmaceutically effective dose of the myostatin siNA conjugates or pharmaceutical compositions is systemically administered to a subject. A pharmaceutically effective dose is that dose required to prevent, inhibit the occurrence, or treat (alleviate a symptom to some extent, preferably all of the symptoms) a disease state. One skilled in the art can readily determine a therapeutically effective dose of a myostatin siNA conjugate to be systemically administered to a given subject, e.g., by taking into account factors, such as the size and weight of the subject, the extent of the disease progression or penetration, the age, health, and sex of the subject, and the route of systemic administration. Generally, an amount between 0.1 µg/kg and 100 mg/kg body weight/day of active ingredients is administered dependent upon potency of the negatively charged polymer. Optimal dosing schedules can be calculated from measurements of drug accumulation in the body of the patient. The myostatin siNA conjugates can be administered in a single dose or in multiple doses.

In one embodiment, the siNA conjugates described herein are systemically delivered to a subject at a dose of between about 0.1 to about 500 mg/kg (mpk). In another embodiment, the siNA conjugates are delivered at a dose of between about 1 to about 200 mpk. In another embodiment, the siNA conjugates are delivered at a dose of between about 1 to about 100 mpk. In another embodiment, the siNA conjugates are delivered at a dose of between about 5 to about 60 mpk. In another embodiment, the siNA conjugates are delivered at a dose of between about 10 to about 50 mpk.

The myostatin siNA conjugates can be administered once monthly, once weekly, once daily (QD), or divided into multiple monthly, weekly, or daily doses, such as, for example, twice daily (BID), three times daily (TID), once every two weeks. Thus, administration can be accomplished via single or divided doses. Persons of ordinary skill in the art can easily estimate repetition rates for dosing based on measured residence times and concentrations of the drug in bodily fluids or tissues.

In addition, the administration can be continuous, e.g., every day, or intermittently. For example, intermittent administration of a myostatin siNA conjugate may be administration one to six days per week, administration in cycles (e.g., daily administration for two to eight consecutive weeks, then a rest period with no administration for up to one week), or administration on alternate days.

Aerosol compositions can be administered into the respiratory system as a formulation that includes particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range can be from 1 to 5 microns. In another embodiment, the particulate range can be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

EXAMPLES

Examples provided are intended to assist in a further understanding of the invention. Particular materials employed, species and conditions are intended to be illustrative of the invention and not limiting of the reasonable scope thereof. Certain starting materials and reagents are either commercially available or known in the chemical scientific or patent literature.

Example 1: Mtsn siRNA siRNA Synthesis— siRNAs were synthesized by methods similar to those previously described (Wincott, F. et al., 1995, *Nucleic Acids Res.* 23:2677-84). For each oligonucleotide duplex, the individual, complementary sense and antisense strands were first synthesized on solid support, such as on controlled pore glass, using commercially available automated oligosynthesizers. The solid support was obtained pre-loaded with the first (3') nucleotide unit of the desired sequence and placed in an appropriate column for the oligosynthesizer. The first nucleotide was linked to the solid support via a succinate linkage and contained a suitable acid sensitive protecting group (trityl, dimethoxytrityl) on the 5'-terminal hydroxyl group. The solid-phase oligosynthesis employed synthetic procedures that are generally known in the art. Elongation of the desired oligomeric sequence went through a cycle of four steps: 1) Acidic deprotection of the 5'-trityl protecting group; 2) Coupling of the next nucleotide unit as the 5'-trityl (or dimethoxytrityl) protected phosphoramidite in the presence of an activating agent, such as S-ethyl-tetrazole; 3) Oxidation of the P(III) phosphite triester to the P(V) phosphate triester by an oxidizing agent, such as iodine; and 4) Capping any remaining unreacted alcohol groups through esterification with an acylating agent, such as acetic anhydride. The phosphoramidites used were either derived from naturally occurring nucleotide units or from chemical modified versions of these nucleotides. Oligonucleotide synthesis cycles were continued until the last (5') nucleotide unit was installed onto the extended oligomer. After the final cycle, the 5'-trityl protecting group may or may not be removed from the oligonucleotide while it remains on the solid support. In some instances, the 5'-terminal trityl was first removed by treatment with an acidic solution.

After deprotection, the solid support was treated with an appropriate base, such as aqueous methylamine, in order to cleave the oligonucleotide from the support, remove the cyanoethyl protecting groups on the phosphates and deprotect the acyl protecting groups on the nucleotide bases. After cleavage of each strand from the solid support, each strand was purified chromatographically with a reversed phase (C18) or anion exchange (SAX) resin. Typically, the oligonucleotide was eluted from SAX resin with a gradient of an inorganic salt, such as sodium chloride. Salt was removed from the purified samples by dialysis or tangential flow filtration.

Each purified oligonucleotide was analyzed for purity by appropriate methods, including reversed phase HPLC, SAX HPLC, and capillary gel electrophoresis. The identity of the oligonucleotide was confirmed by mass spectrometry, using an ionization technique such as ESI or MALDI. The yields of each oligonucleotide were assessed by UV (260 nm) with a theoretically derived extinction coefficient.

The corresponding sense and antisense strands were annealed by mixing an equimolar amount of each material. The appropriate amounts of each strand were approximated by UV (260 nm) measurements and theoretical extinction coefficients. After the annealing process, the extent of duplex formation and the presence of any excess single strand material were assessed by an appropriate chromatographic method, such as RP-HPLC or SAX. When appropriate, the sample was adjusted with additional amounts of one of the two strands in order to completely anneal the remaining excess single strand. The final duplex material was lyophilized prior to delivery for further biochemical or biological testing.

Cells and Reagents—

Mouse hepatoma Hepa 1-6 cell line was obtained from the American Type Tissue Collection (Cat # CRL-1830). Cells were grown in Dulbecco's Modified Eagle Medium, High Glucose with Glutamax™ (Invitrogen Cat #10566024) adjusted to 1 mM sodium pyruvate (Invitrogen Cat #11360070 and supplemented with 10% fetal bovine serum. Streptomycin and penicillin were added to the media at 100 μg/mL and 100 U/mL, respectively. Cells were cultured at 37° C. in the presence of 5% $CO_2$.

Generation of Luciferase Reporter Constructs— siRNAs were screened using the psiCHECK2 dual luciferase reporter system. The luciferase reporter plasmids used were derived from psiCHECK2 vector (Promega, Cat# C8021). Through de novo synthesis, the full length transcript of mouse myostatin (NCBI GenBank RefSeq NM_010834) was cloned into the XhoI/NotI sites of the vector.

In Vitro Screening of siRNAs—

Hepa1-6 cells were seeded in 96-well plates at a density of 10,000 cells per well and incubated at 37° C. After 24 hours, the cells were co-transfected with siRNAs and the MSTN luciferase reporter plasmid using Lipofectamine 2000 reagent (Life Technologies, Cat#11668019). Primary screens were performed by co-transfecting siRNAs with the MSTN plasmid at final concentrations of 10 nM and 0.6 ng/μL, respectively. The cells were incubated at 37° C. and culture medium was replaced with fresh media 24 hours post-transfection. After an additional 24 hour incubation, reporter Renilla luciferase and control firefly luciferase activities were measured using Dual-Glo Luciferase Assay System (Promega, Cat # E2940). Renilla luciferase activity of each well was divided by firefly luciferase activity from the same cell to normalize for different transfection efficiencies across different wells. The normalized luciferase activities produced by the Mstn siRNAs were further divided by the normalized luciferase activity generated by non-targeting control siNA to calculate the percent knockdown (% KD) of reporter expression. All calculations of IC50s were performed using R.2.9.2 software. The data were analyzed using the sigmoidal dose-response (variable slope) equation for simple ligand binding.

Results—

Four unique, unconjugated siRNAs that target mouse Mstn mRNA sequence and a non-targeting control siRNA were synthesized. The target nucleotide sequences of the four Mstn siRNAs are set forth in Table 2a ("target sequence").

TABLE 2a

Mstn target sequences (5' to 3'), noting the assigned mouse target site number (column 2) and the sequence identification number (SEQ ID NO.) (column 3).

| Target Sequence | Target Site (mouse) | SEQ ID NO: |
|---|---|---|
| AUGGCAAAGAACAAAUAAU | 1167 | 1 |
| GGCAAAGAACAAAUAAUAU | 1169 | 2 |
| ACUCCAGAAUAGAAGCCAU | 255 | 3 |
| UUUGGAAGAUGACGAUUAU | 421 | 4 |

TABLE 2b

Various myostatin-related siNA sense (passenger) and antisense (guide) sequences (5' to 3') corresponding to the selected target site sequences in Table 2a. Antisense sequences are readily identified as being complementary to the sense sequence shown. The SEQ ID NOs listed in column 2 correspond to the sense sequences listed in column 3. The SEQ ID NOs listed in column 5 correspond to the antisense sequences listed in column 4.

| Target Site (mouse) | SEQ ID NO: | Sense (Target) Sequence (5' to 3') | Antisense Sequence (5' to 3') | SEQ ID NO: |
|---|---|---|---|---|
| 1167 | 1 | AUGGCAAAGAACAAAUAAU | AUUAUUUGUUCUUUGCCAU | 18 |
| 1169 | 2 | GGCAAAGAACAAAUAAUAU | AUAUUAUUUGUUCUUUGCC | 19 |
| 255 | 3 | ACUCCAGAAUAGAAGCCAU | AUGGCUUCUAUUCUGGAGU | 20 |
| 421 | 4 | UUUGGAAGAUGACGAUUAU | AUAAUCGUCAUCUUCCAAA | 21 |

The nucleotide sequences of the Mstn siRNAs and the non-targeting control siRNA are indicated in Table 3. The double-stranded siRNA molecules within Table 3 contain a sense strand (also known as the passenger strand) and an antisense strand (also known as the guide strand), wherein each strand is comprised of 21 nucleotides (position 1 (5') to position 21 (3')) and contains both internal and terminal chemically-modified nucleotides. The name of each siRNA molecule is provided in column 1 and corresponds to the mouse Mstn mRNA region to which the molecule is targeted. Column 2 of Table 3, "Strand", indicates whether the particular sequence in the indicated row is the sense (S) or antisense (A/S) strand of the duplex. Column 3 of Table 3, "5-position 1 nuc," describes nucleotide position 1 of the sense and antisense strands of the indicated siRNA molecules, each comprising of a nucleotide with a 5' cap moiety. The chemical structure of each 5'-position 1 nucleotides is provided in Table 6a, infra. The nucleotide sequence spanning positions 2-20 for each of the sense and antisense strands of the siRNA molecules is described in column 4 of Table 3, wherein the individual nucleotides are separated by a semicolon. The chemical structure of each nucleotide indicated within column 4 is provided for in Table 6b, infra. The 5th column of Table 3, "Nuc position 21-3'," represents the 3' most nucleotide of the sense or antisense strand of the siRNA, each represented by "omeU-iB" or "omeUSup" (for structures, see Table 6c, infra). The SEQ ID NO: for each strand of the siRNA molecules of Table 3 (positions 1-21) is provided in column 6. Each siRNA molecule in Table 3 has 3' overhangs consisting of 2 nucleotides at both ends of the molecule.

Example 2: Mtsn siRNA Cholesterol Conjugates

Cholesterol Conjugation—

A single cholesterol entity was attached to the 3' end of the sense strand of each siRNA molecule described in Table 3. For the preparation of oligonucleotides with a cholesterol unit on the 3'-terminus, deoxycytidylyl-deoxyguanosine (CpG) (see Table 6d, infra, for structure) with a preloaded cholesterol succinate, which also contained a dimethoxytrityl (DMT) protected primary alcohol, was used for synthesis of the corresponding oligonucleotide sequence (see

TABLE 3

Mstn siRNA sequences

| siRNA name | Strand | 5'-position 1 nuc | Nucleotide sequence - position 2 to position 20 | Nuc position 21-3' | SEQ ID NO: |
|---|---|---|---|---|---|
| Mstn: 1167 | S | 6amiL-iB-fluA | omeU; fluG; omeG; fluC; omeA; fluA; omeA; fluG; omeA; fluA; omeC; fluA; omeA; fluA; omeU; fluA; omeA; fluU; omeUs | omeU-iB | 5 |
| | A/S | vinylP-moeT | fluU; omeU; fluA; omeU; fluU; omeU; fluG; omeU; fluU; omeC; fluU; omeU; fluU; omeG; fluC; omeC; fluA; omeU; omeUs | omeUSup | 6 |
| Mstn: 1169 | S | 6amiL-iB-fluG | omeG; fluC; omeA; fluA; omeA; fluG; omeA; fluA; omeC; fluA; omeA; fluA; omeU; fluA; omeA; fluU; omeA; fluU; omeUs | omeU-iB | 7 |
| | A/S | vinylP-moeT | fluU; omeA; fluU; omeU; fluA; omeU; fluU; omeU; fluG; omeU; fluU; omeC; fluU; omeU; fluU; omeG; fluC; omeC; omeUs | omeUSup | 8 |
| Mstn: 255 | S | 6amiL-iB-fluA | omeC; fluU; omeC; fluC; omeA; fluG; omeA; fluA; omeU; fluA; omeG; fluA; omeA; fluG; omeC; fluC; omeA; fluU; omeUs | omeU-iB | 9 |
| | A/S | vinylP-moeT | fluU; omeG; fluG; omeC; fluU; omeU; fluC; omeU; fluU; omeC; fluU; omeG; fluG; omeA; fluU; omeU; fluG; omeU; omeUs | omeUSup | 10 |
| Mstn: 421 | S | 6 amiL-iB-fluU | omeU; fluU; omeG; fluG; omeA; fluA; omeG; fluA; omeA; fluC; omeG; fluA; omeU; fluU; omeA; fluU; omeUs | omeU-iB | 11 |
| | A/S | vinylP-moeT | fluU; omeA; fluA; omeU; fluC; omeG; fluU; omeC; fluA; omeU; fluC; omeU; fluU; omeC; fluC; omeA; fluA; omeA; omeUs | omeUSup | 12 |
| Placebo: 5 | S | 6 amiL-iB-fluG | omeU; fluC; omeG; fluC; omeC; fluU; omeU; fluA; omeU; fluA; omeU; fluC; omeG; fluG; omeU; fluC; omeG; fluA; omeUs | omeU-iB | 13 |
| | A/S | vinylP-moeT | fluC; omeG; fluA; omeC; fluC; omeG; fluA; omeU; fluA; omeU; fluA; omeA; fluG; omeG; fluC; omeG; fluA; omeC; omeUs | omeUSup | 14 |

Each siRNA (10 nM) was co-transfected along with a Mstn luciferase reporter plasmid (0.6 ng/μl) into cells, and luciferase activity was measured after 48 hours as a reflection of mRNA knockdown (KD). The four siRNAs show a minimum of 90% Mstn mRNA knockdown and 1050 values less than 0.016 nM (see Table 4).

TABLE 4

Mstn siRNA in vitro knockdown activity

| siRNA | Max mRNA KD (%) | IC50 (nM) |
|---|---|---|
| Mstn: 1167 | 91 | 0.007 |
| Mstn: 1169 | 90 | 0.005 |
| Mstn: 255 | 94 | 0.004 |
| Mstn: 421 | 95 | 0.016 |

Example 1). Typically, the final 5'-DMT protecting group was removed during oligosynthesis. The oligonucleotide was then cleaved from the CpG by treatment with a basic solution, such as aqueous methylamine, and purified by chromatography with a reversed phase resin, such as C18. This purified oligo was annealed to its corresponding complementary strand to prepare the desired oligonucleotide duplex.

Animals—

Female CD-1 mice were obtained from Charles River and were between 8-9 weeks old at time of study. Mice were maintained on a 12-hour light and dark cycle with al libitum access to water and standard chow diet (no. 5001; LabDiet). Control and experimental cholesterol-conjugated siRNAs were administered to mice by tail vein injections at indicated dosages. All animal studies were conducted at Merck Research Laboratories in an AAALAC-accredited West Point, Pa. animal facility using protocols approved by the Institutional Animal Care and Use Committee (IACUC).

Quantitative Real-Time PCR Analysis—

Mice were sacrificed and tissues were homogenized in Trizol (Invitrogen), extracted in 1-bromo-2-chloropropane (Acros Organics), and total RNA was isolated using the MagMax RNA isolation method (Ambion). RNA (125 ng) was reverse transcribed using the High Capacity cDNA Reverse Transcription kit (Applied Biosystems, Cat #4368813). Taqman qPCR analysis was performed using an ABI 7900 Real-Time PCR System using TaqMan Fast Advanced Master Mix (Applied Biosystems, Cat#4444555). All Taqman probes and primers were purchased from Applied Biosystems as pre-validated sets: mouse PPIB Assay ID Mm00478295_ml; mouse Mstn Assay ID Mm01254559_ml. Taqman data analysis was performed on an ABI 7900 Real-Time PCR System, as described previously (Tadin-Strapps, M. et al., 2011, *J. Lipid Res.* 52:1084-1097).

Serum Analysis of Myostatin Protein—

Blood was collected by tail vein collection, and serum was collected at the specified time points and analyzed using the GDF-8/Myostatin Quantikine ELISA kit (R&D, Cat # DGDF80). Briefly, serum samples were activated as described in manufacturer protocol, with the exception that the final activated serum sample had an additional 1:2 dilution in calibrator diluent before assaying.

Results—

In vivo efficacy studies in CD-1 mice were performed using the four Mstn siRNA molecules of Table 3, each of which is conjugated to a single cholesterol moiety at the 3' most nucleotide of the sense (passenger) strand. Mice were injected intravenously with 15 mpk siRNA, and Mstn mRNA knockdown was assessed in the gastrocnemius muscle after 72 hours (FIGS. 1A and 1B). Reduction of Mstn expression was seen, especially with Mstn:1169 and Mstn:1167 cholesterol conjugates. The Mstn:1169 cholesterol conjugate was selected for use in follow-up siRNA optimization and functional studies.

Figure 2A:
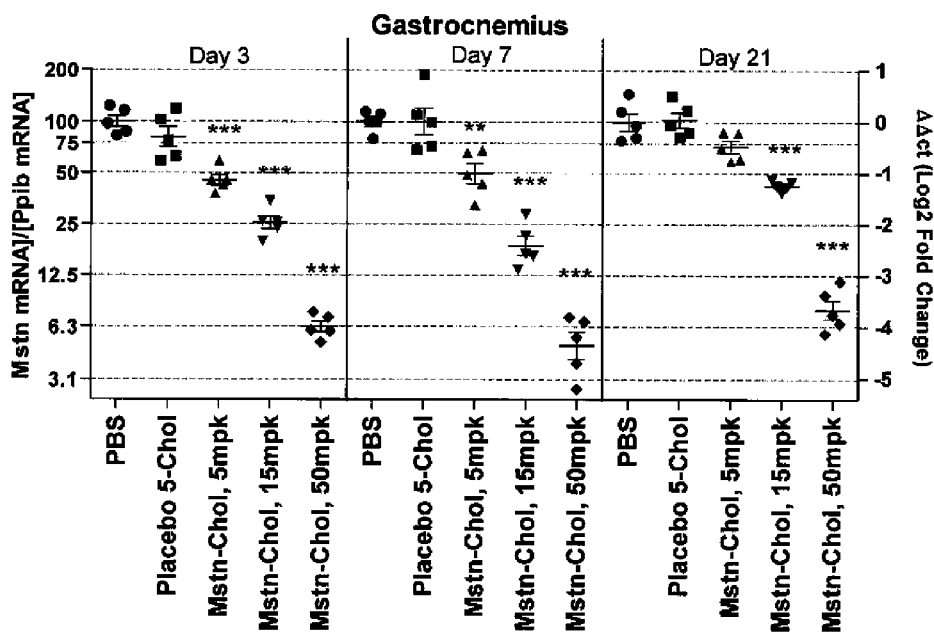
FIG. 2: In vivo dose titration and duration of myostatin mRNA knockdown (KD) by Mstn-cholesterol siRNA. Mstn: 1169-cholesterol ("Mstn-chol") siRNA was tested in CD-1 mice (n=5) at 5, 15, and 50 mpk, in addition to PBS and Placebo 5 non-targeting controls (50 mpk) by i.v. injection. Mstn mRNA expression was determined based on ΔΔCt calculations, relative to PBS, in gastrocnemius (A), tricep muscles (B), and EDL (C), at day 3, 7, and 21 post-injection. (D) Serum Mstn protein levels were measured at indicated time points. *, P<0.05; , P<0.01; *, P<0.001 (by one-way ANOVA).
Figure 2B:
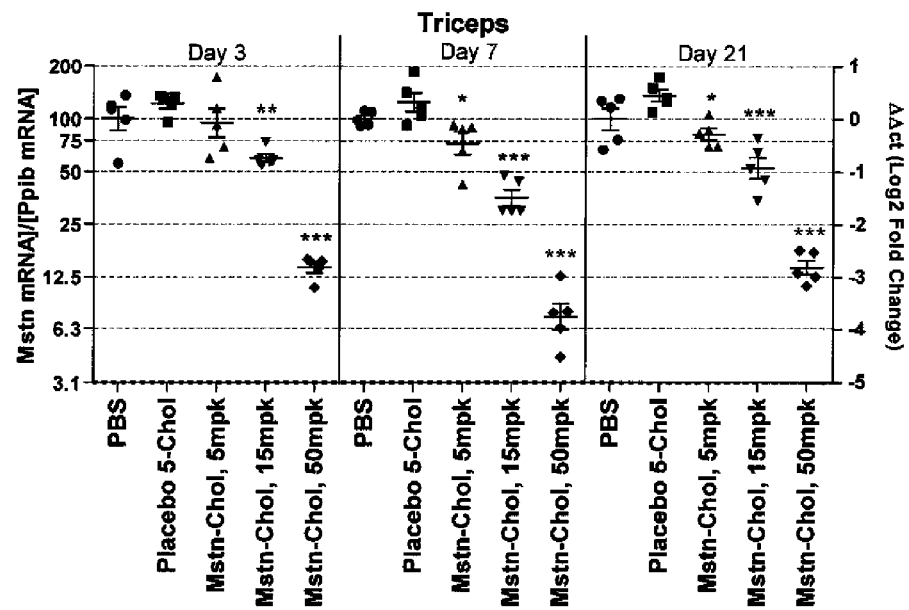
Figure 2C:
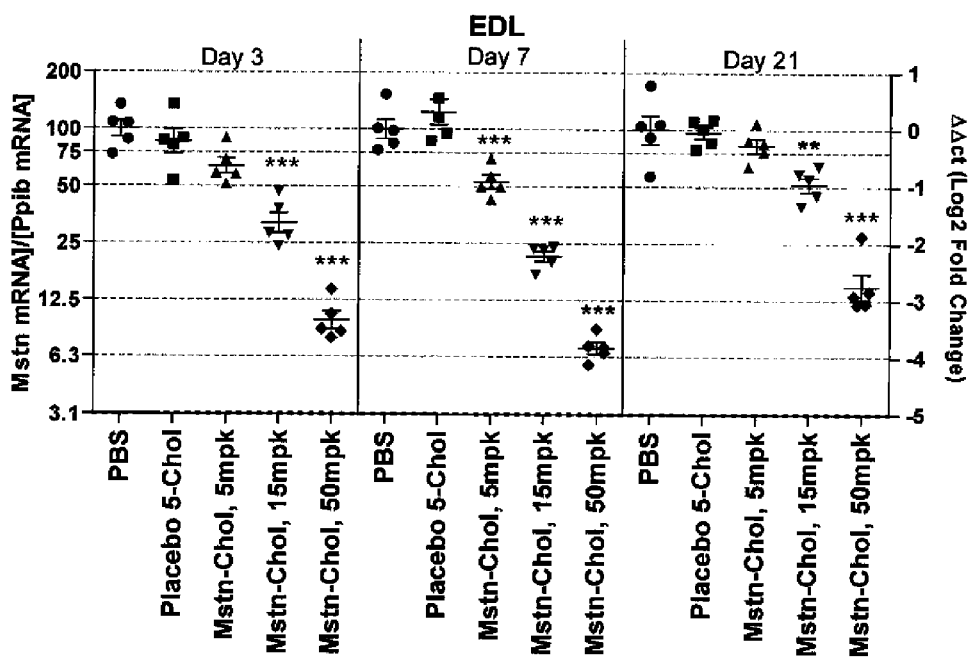
Figure 2D:
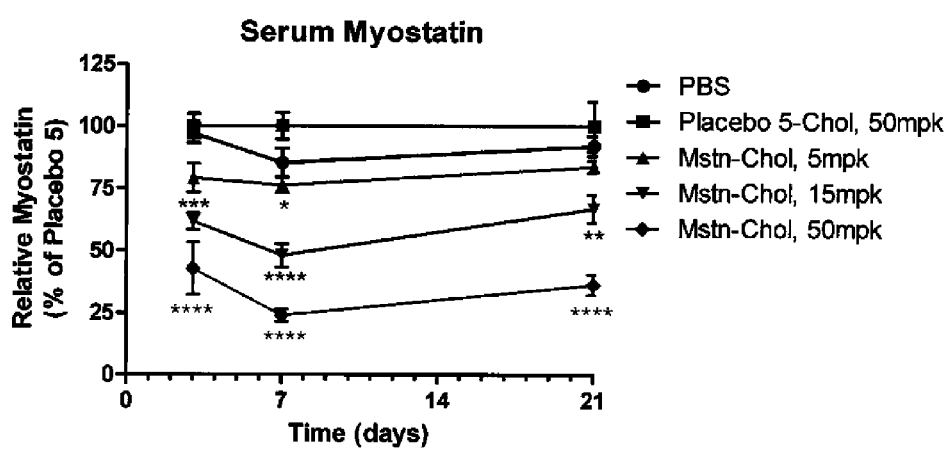

In order to examine the potency and efficacy of the Mstn:1169-cholesterol conjugate, mice were treated with a single injection of the conjugate at 5, 15, and 50 mpk. Mstn mRNA and circulating protein levels were measured at various time points (FIG. 2). Mstn:1169-cholesterol treatment caused a dose-dependent knockdown in Mstn mRNA in gastrocnemius (FIG. 2A), tricep (FIG. 2B) and EDL (FIG. 2C) muscles, demonstrating greater than 8-fold difference in potency between the 5 mpk and 50 mpk doses. Maximum knockdown (KD) was observed with the 50 mpk dose at day 7, showing 90-95% mRNA knockdown in all three muscles and 75% knockdown of circulating protein levels (FIG. 2D). Mstn gene silencing with 50 mpk siRNA was between 88-95% KD in gastrocnemius, triceps and spinotrapezius muscles (data not shown), which are mixed fiber type muscles, as well as in the EDL muscle, a predominantly type II fiber muscle. Mstn mRNA knockdown effects could not be determined in the soleus muscle due to low Mstn mRNA levels in this muscle (data not shown). Mstn siRNA also displays an extended duration of silencing, maintaining 90-95% mRNA KD and 65% serum Mstn protein levels for 21 days after 50 mpk dosing. There was no evidence of liver toxicity and muscle damage at all doses examined, as determined by monitoring serum ALT/AST and muscle creatine phosphokinase, respectively (data not shown).

Example 3: Prolonged Mstn Knockdown Increases Muscle Size and Alters Muscle Fatigue Profile Body Composition—

Animal body composition was measured by quantitative magnetic resonance spectroscopy using an EchoMRI instrument (Echo Medical Systems, Houston, Tex.), in order to determine lean/fat mass. Measurements were made 20 days after initiation of siRNA dosing.

Micro-CT Imaging and Data Analysis—

Using the LaTheta micro-CT (LaTheta LCT-100A™, Aloka, Echo Medical Systems, Houston, Tex.), a stack of 10 slices was scanned between the knee and fibula-tibia junction. Images were analyzed as previously described (Weber, H. et al., 2012, *J. Appl. Physiol.* 112:2087-98) to find the largest cross sectional area (CSA) of whole muscle in the lower leg. Mice were scanned at day-1 with respect to siRNA dosing, and also scanned at day 3, 7, 14 and 21.

In Situ Muscle Function Assay—

A custom build in situ assay system, as previously described (see Weber, H. et al., supra), was performed 21 days after siRNA dosing. Briefly, the Achilles tendon of an anesthetized animal was connected to the lever of a combined servomotor/force transducer unit. Electric impulses were delivered via the sciatic nerve to stimulate the muscles of the lower leg to contract, while the resulting force was recorded. Tetanic stimulation trains of 50 ms length, containing 4 mA square pulses of 0.1 ms duration at 100 Hz, were repeated at a frequency of 0.8 Hz for 300 s. A constant baseline tension of 0.1 N was reestablished between stimulations. After completion of the in situ assay, the hind limb muscles were collected for weighing and histology.

Several parameters representing the fatigue envelopes were extracted from a double sigmoidal curve fit, including maximum force ($F_{max}$), intermediate force ($F_o$), minimum force ($F_{min}$), early fatigue force ($F_{max}$-$F_o$), late fatigue force ($F_o$-$F_{min}$), maximal slope of early fatigue ($S_1$) and late fatigue ($S_2$) and time constants of early ($\tau_1$) and late fatigue ($\tau_2$) forces.

Measurement of Tibia Bone Lengths—

After sacrificing mice, each hindlimb was stored in 70% ethanol overnight. Next day, legs were stripped of muscle and tissue and length was measured using a digital caliper.

Quantitation of Myofiber Size and Number—

In order to detect muscle fiber cell size, laminin staining was performed on gastrocnemius muscle 21 days-post siRNA/control treatment. A transverse cross-section made through the widest region of the gastrocnemius muscle was fixed in 10% formalin overnight. Muscle was paraffin-embedded and sectioned (5 µm) by standard methods. Sections underwent heat-induced antigen retrieval using citrate buffer (EZAR1, BioGenx #HJ521-XAK) at 103° C. for 10 minutes using a BioGenex EZ-Retriever Microwave. After PBS washes, sections were incubated at room temperature for 1 hour with a polyclonal Rabbit anti-Laminin antibody at a 1:100 dilution (Abcam, cat # ab11575). A goat anti-rabbit A555 immunofluorescent secondary antibody was applied after further PBS washes (Invitrogen #A21429), and the slides were mounted using ProlongGold with Dapi (Invitrogen #P36935). Images were captured on a BX-63 Olympus Microscope using a Hamamatsu ORCA-R2 camera and cellSens Dimension 1.7 software (Olympus). Muscle fiber area and total number of fibers were quantitated on the muscle cross-section using Definiens software. Regions out of focus were eliminated from analysis prior to the segmentation of the image. A multi-resolution algorithm was used to extract the muscle fiber and the endomysiums in the remaining muscle section. Fiber area was determined from 12 mice per group, with 1200-7000 cell counts/mouse. Mean fiber size and size frequency distribution of muscle fibers is shown.

Results—

Figure 3A:
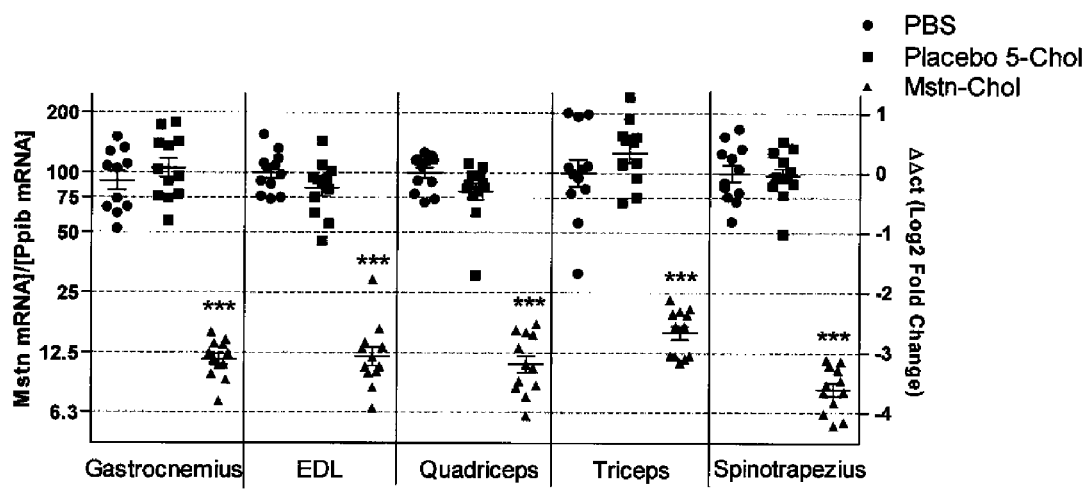
FIG. 3: Long-term myostatin knockdown (KD) leads to increase in muscle size. Mstn:1169-cholesterol siRNA (50 mpk) was injected intravenously into CD-1 mice (n=12), in addition to PBS and Placebo 5 non-targeting controls. (A) Mstn mRNA levels, determined based on ΔΔCt calculations, relative to PBS, in gastrocnemius, EDL, quadriceps, triceps and spinotrapezius muscles at day 21 post-injection. (B) Serum Mstn protein levels, determined for the duration of the study. (C) Leg muscle size (maximum cross-sectional area), monitored for the duration of the study and quantitated from a series of 10 micro-CT images using a custom MATLAB and Definiens Developer XD software algorithm. (D) Gastrocnemius muscle weight of rested leg and exercised leg (used in situ muscle function assay) at day 21. (E) Mean fiber cross-sectional area of gastrocnemius muscle. (F) Mean total number of muscle fibers in gastrocnemius muscle. (G) Size frequency distribution of muscle fibers in gastrocnemius muscle. (H) Body weight measurements, determined for the duration of the study. (I) Body composition analysis by qNMR (EchoMRI) at day 20. *, P<0.05; , P<0.01; *, P<0.001 ****, P<0.0001 (by one-way ANOVA (a-b) or two-way ANOVA (c-h))
Figure 3B:
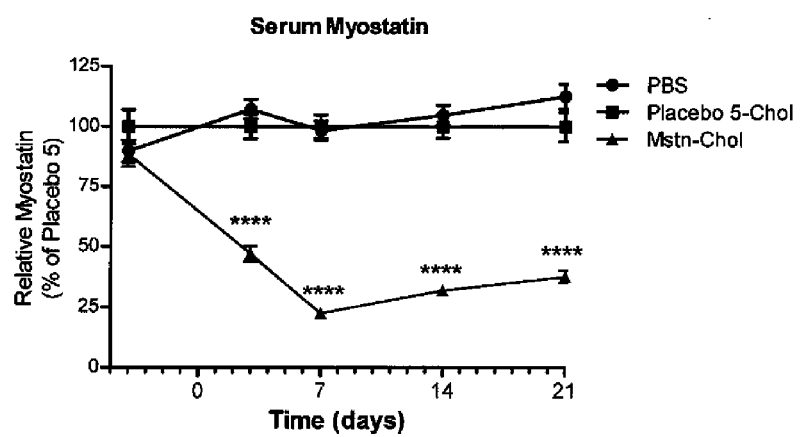
Figure 3C:
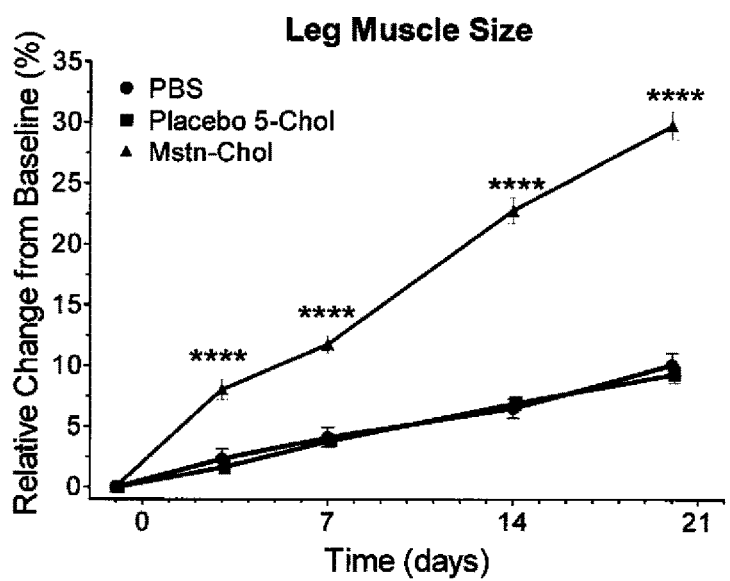
Figure 3D:
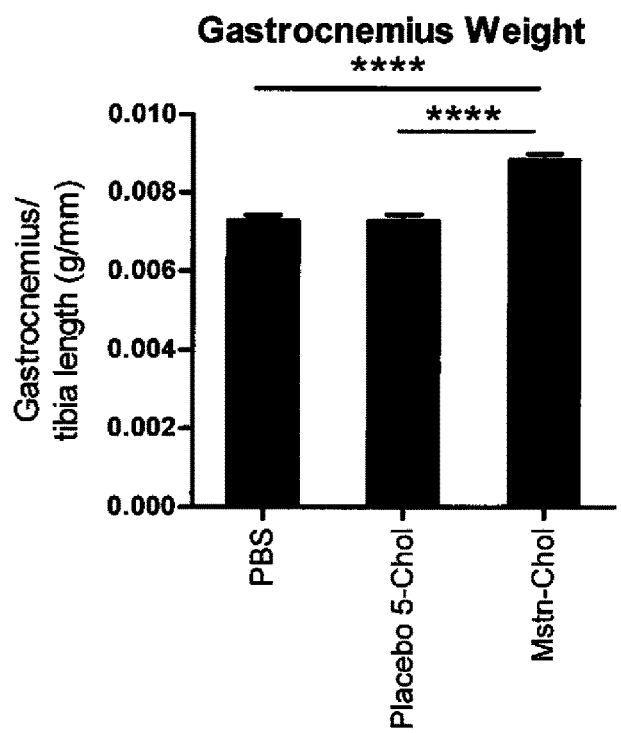
Figure 3E:
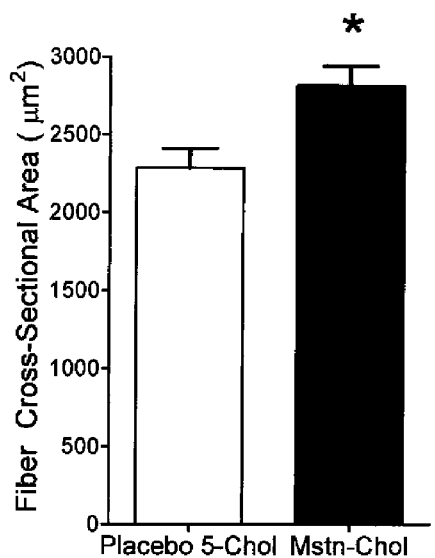
Figure 3F:
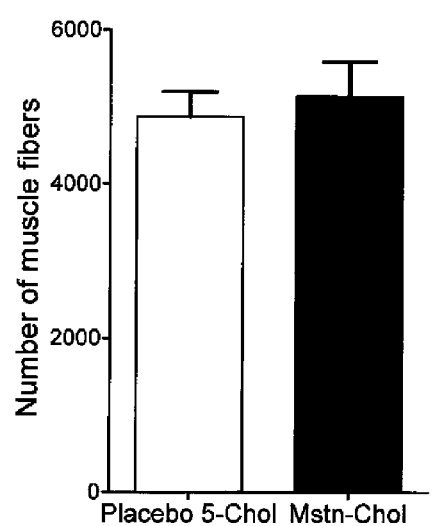
Figure 3G:
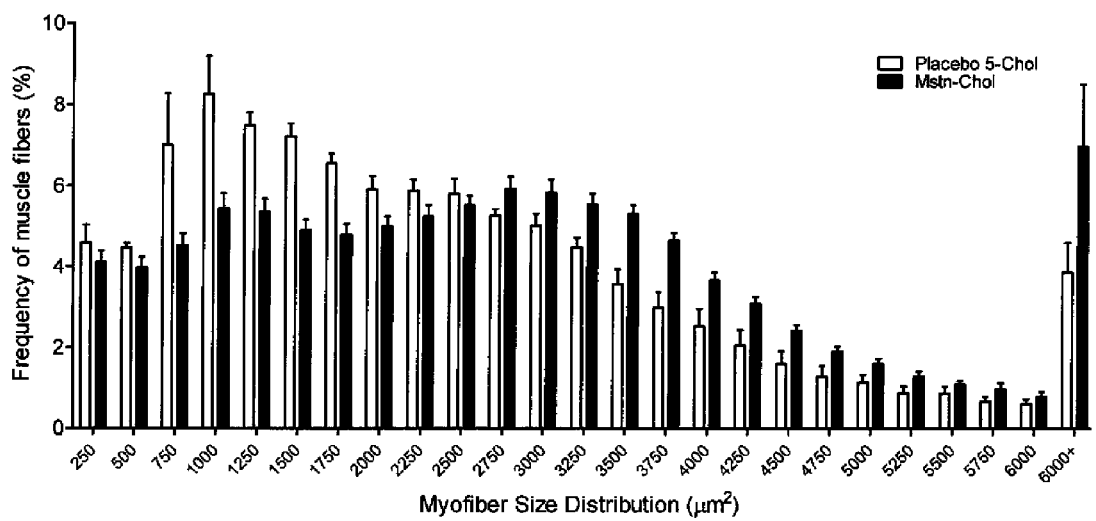
Figure 3H:
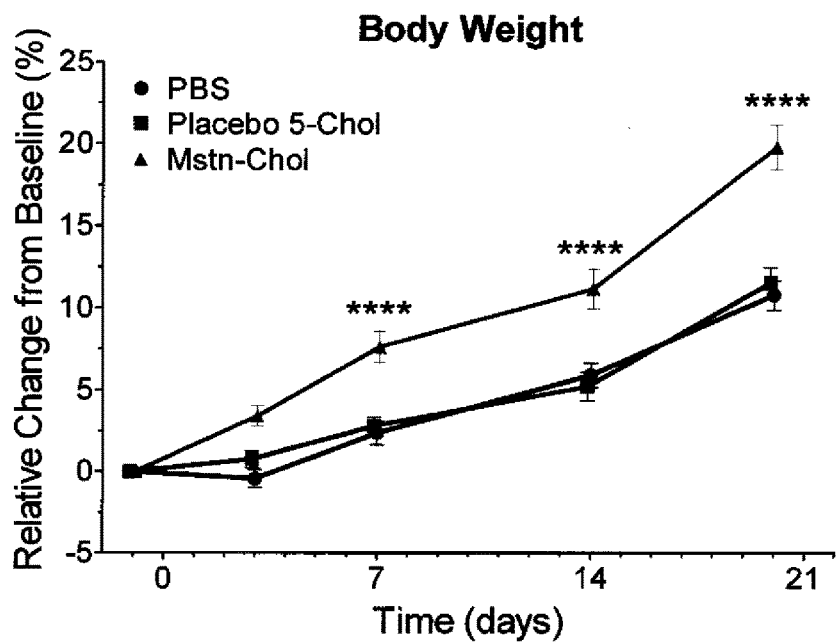
Figure 3I:
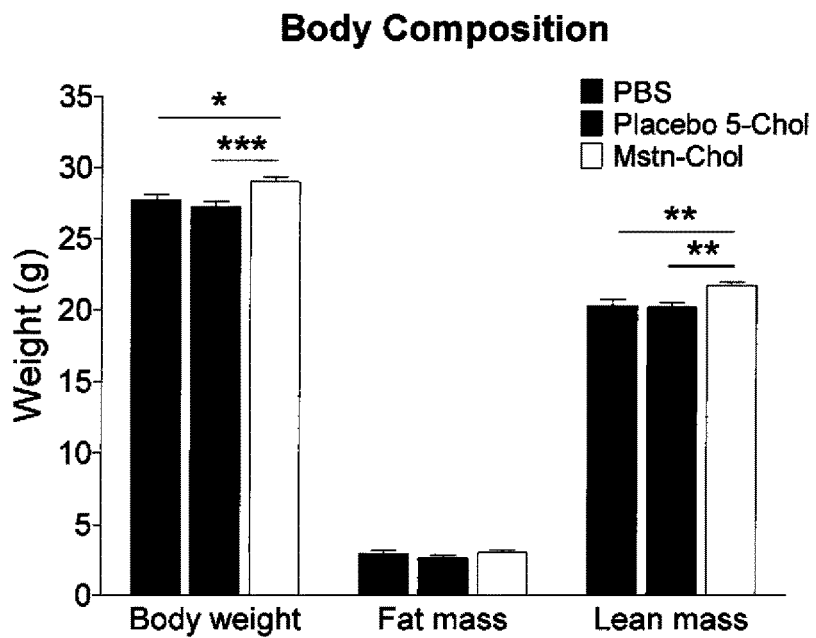

Since Mstn is known to have a major inhibitory role in muscle growth, the effects of Mstn silencing on muscle mass and function was examined. In order to achieve maximum Mstn knockdown, mice were treated with a single i.v. 50 mpk dose of the Mstn:1169-siRNA-cholesterol conjugate (see Examples 1 and 2, supra) or controls. After 21 days, mice treated with the Mstn siRNA conjugate showed 85-90% Mstn mRNA knockdown in gastrocnemius, EDL, quadriceps, triceps and spinotrapezius muscles (FIG. 3A). In addition, circulating levels of Mstn protein were sustained at >65% reduction through day 21 (FIG. 3B). Muscle size was monitored in both hind limbs of mice by micro-CT at 3, 7, 14 and 20 days after dosing. Maximum muscle cross-sectional area (CSA) for each leg, representative of plantarflexor muscle group, was determined by quantitating a series of 10 slices using a custom MATLAB and Definiens Architect XD software algorithm. Quantitation results indicate a significant increase in muscle size by systemic Mstn siRNA-cholesterol treatment as early as 3 days after initiation of dosing and up to a 20% increase in leg muscle size by day 21 (FIG. 3C). This data is supported by gastrocnemius muscle weights at day 21/22, which also show ~20% increase in the weights of both rested and exercised gastrocnemius muscle by Mstn-chol treatment in comparison to control mice (FIG. 3D) Laminin immunofluorescent staining of a cross-section of gastrocnemius muscle showed that the average fiber cross-sectional area was increased, while the total number of fibers was unaffected by Mstn-chol treatment (FIG. 3E, mean fiber area; FIG. 3F, mean fiber number; FIG. 3G, size frequency distribution). In addition to the significant increase in muscle size observed in mice treated with the Mstn siRNA-cholesterol conjugate, body weight measurements also indicate approximately 10% increase by day 20 (FIG. 3H). Body composition analysis, as determined by quantitative NMR, reveals that this increase in body weight is attributed to an increase in lean mass (FIG. 3I).

Figure 4:
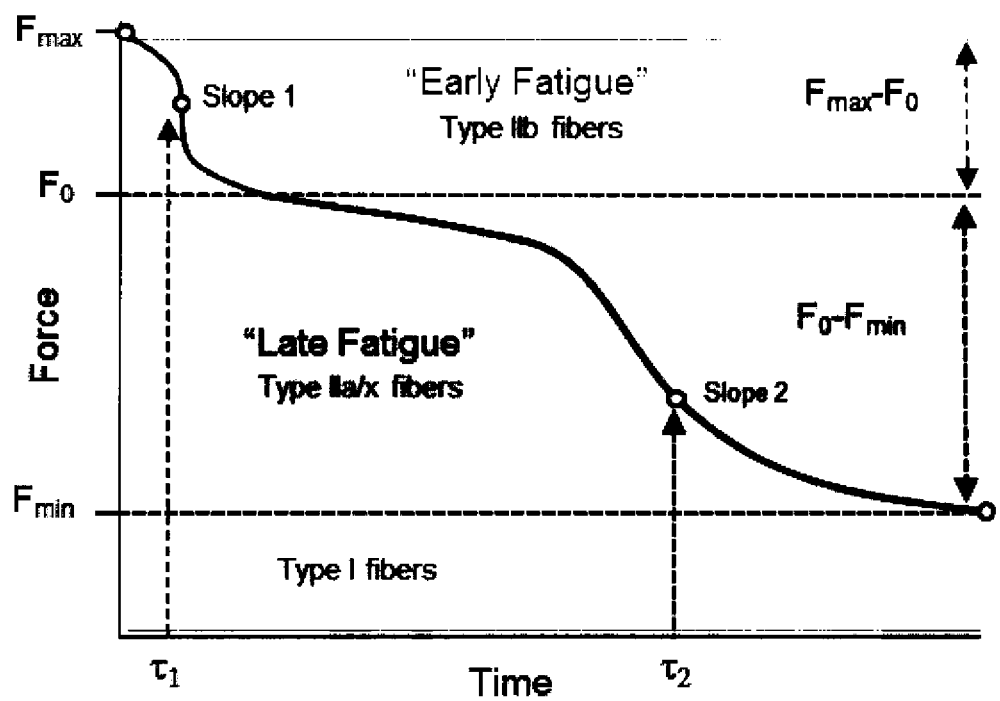
FIG. 4: Example of a muscle fatigue curve. Fatigue curves exhibit three stages of muscle fatigue: early fatigue, late fatigue and a non-fatigable stage. "Early fatigue" is represented by $F_{max}-F_0$, typically representative of type IIb fibers, which use creatine phosphate as an energy source. This stage is followed by "late fatigue" ($F_0-F_{min}$), typically representative of type IIa/x fibers, which use glycogen as an energy source. The final stage of the fatigue curve is the "non-fatigable" stage ($F_{min}$), which is indicative of type I fibers, which use fatty acids as an energy source.

In order to assess potential changes to the strength and fiber type composition of skeletal muscle as a result of siRNA-mediated gene silencing of Mstn, muscle fatigue response to exercise was assayed in an in situ muscle function assay where repeated isometric contractions are induced by electrostimulation. Since skeletal muscle consists of different fiber types, which exhibit different contractile properties and differential energy source usage, changes in muscle performance can be determined by changes in several functional parameters in muscle fatigue curves, as described previously (Weber, H. et al., 2012, supra). Briefly, fatigue curves exhibit three stages of muscle fatigue: early fatigue, late fatigue and a non-fatigable stage (FIG. 4). "Early fatigue" is represented by $F_{max}$-$F_0$, indicative of type IIb fibers, which are strong, fast, fatigue very quickly and use creatine phosphate as an energy source. This stage is followed by "late fatigue" ($F_0$-$F_{min}$), primarily indicative of type IIa/x fibers, which are strong, fast, more fatigue-resistant and use glycogen as an energy source. The final stage of the fatigue curve is the "non-fatigable" stage ($F_{min}$), which is marked type I fibers, which are weak, slow, non-fatigable and use fatty acids as an energy source.

Figure 5A:
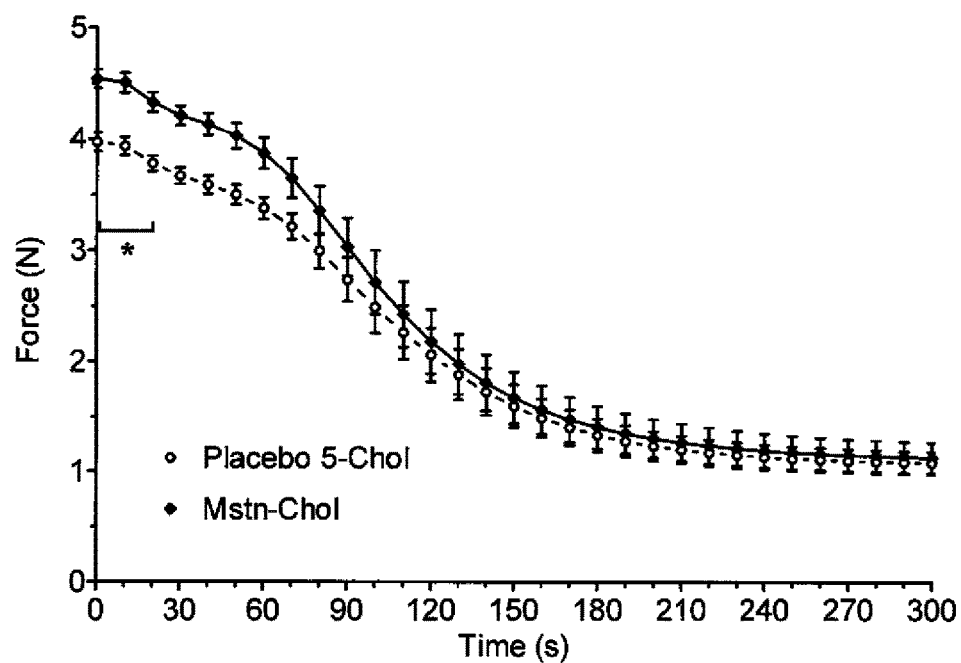
FIG. 5: Long-term myostatin knockdown leads to changes in muscle function. Mstn:1169 siRNA-cholesterol conjugate or Placebo 50-cholesterol non-targeting siRNA control (50 mpk) were injected intravenously into CD-1 mice (n=12). Muscle fatigue curves, force (A) or specific force (B), were generated from in situ muscle function assay performed on day 21/day 22 (n=9 total). Function parameters calculated from the indicated fatigue curve are plotted below each curve in (A) and (B). Filled in bars indicate a statistical significant change in the specified parameter between Mstn siRNA-cholesterol conjugate and Placebo 5-cholesterol treatment. *, P<0.05; , P<0.01; *, P<0.001 ****, P<0.0001 (by one-way ANOVA (a-b) or two-way ANOVA (c-h))
Figure 5A:
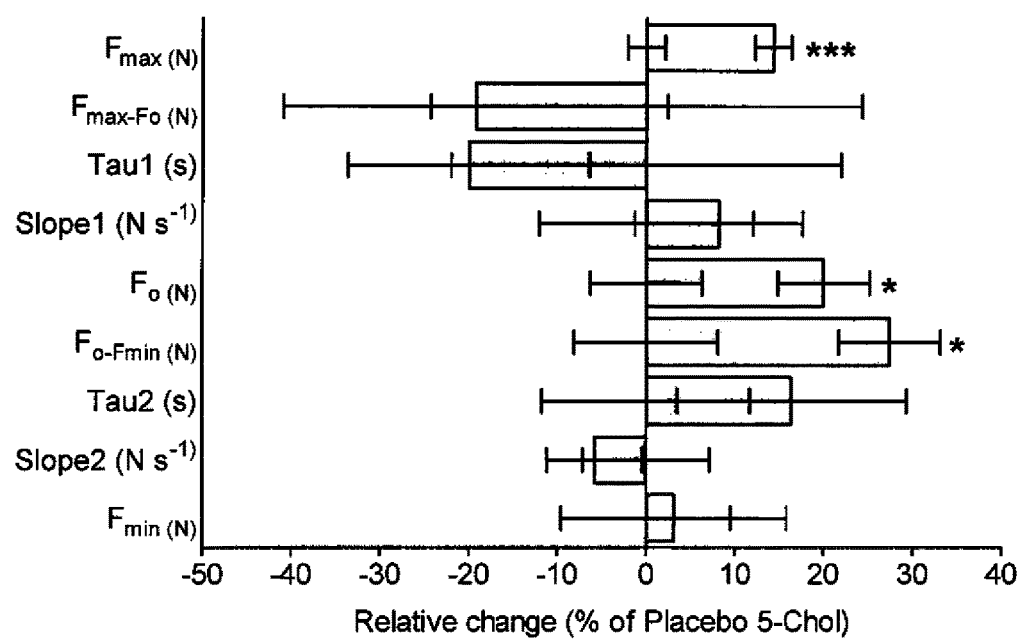

Mstn knockdown results in increased $F_{max}$ and $F_0$, but since $F_{max}$-$F_0$ remains unchanged, the "early fatigue" stage is unaffected (FIG. 5A). While there is no significant change in $F_{min}$, $F_0$-$F_{min}$ is increased, suggesting an increase in "late fatigue" indicative of increased contractile force. This data suggests that Mstn knockdown results in a change in type IIa/x fibers, due to a potential increase in the size, quantity and/or strength of the fibers. In addition, there is no change in any of the parameters associated with the timing of the fatigue stages ($\tau_1$, $\tau_2$, $S_1$, $S_2$), suggesting that fuel availability and usage are unaffected.

Figure 5B:
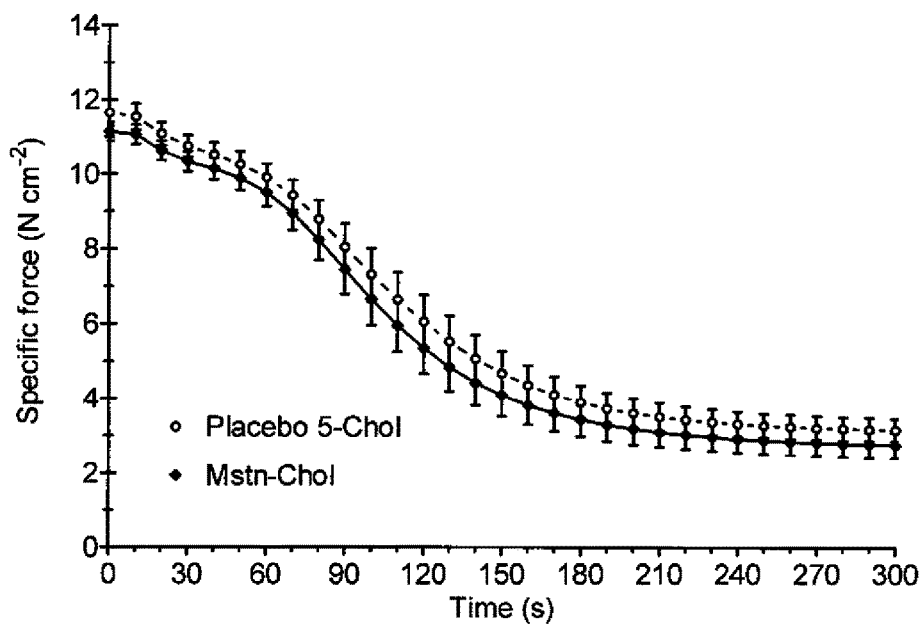
Figure 5B:
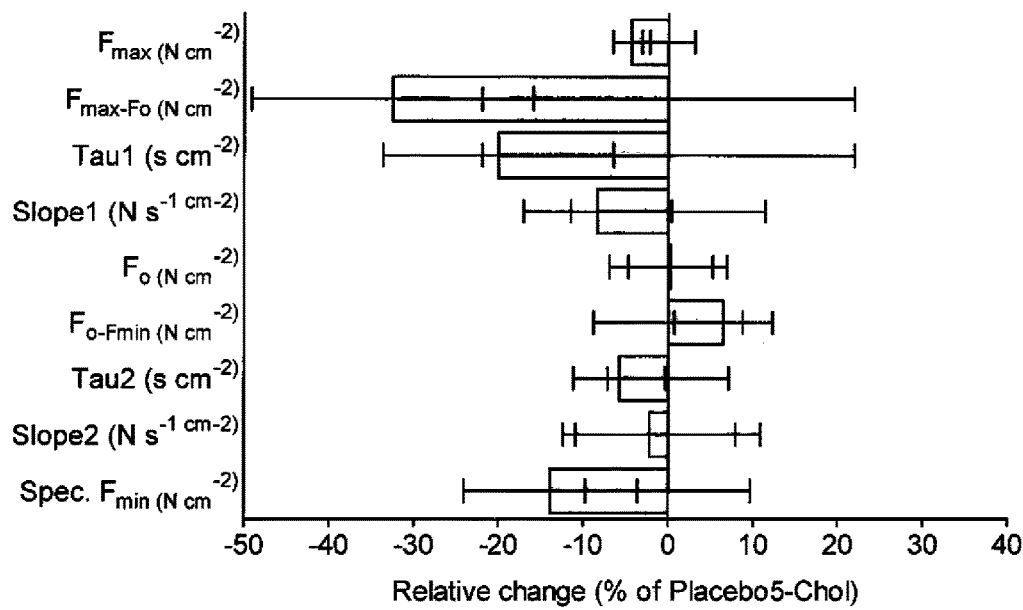

In order to determine changes to muscle quality, "specific force" was calculated by normalizing muscle contractile force to cross-sectional area (CSA) (FIG. 5B). There was no significant difference in specific force or any additional functional parameter in response to Mstn knockdown, suggesting that there is no effect on muscle quality.

Figure 6:
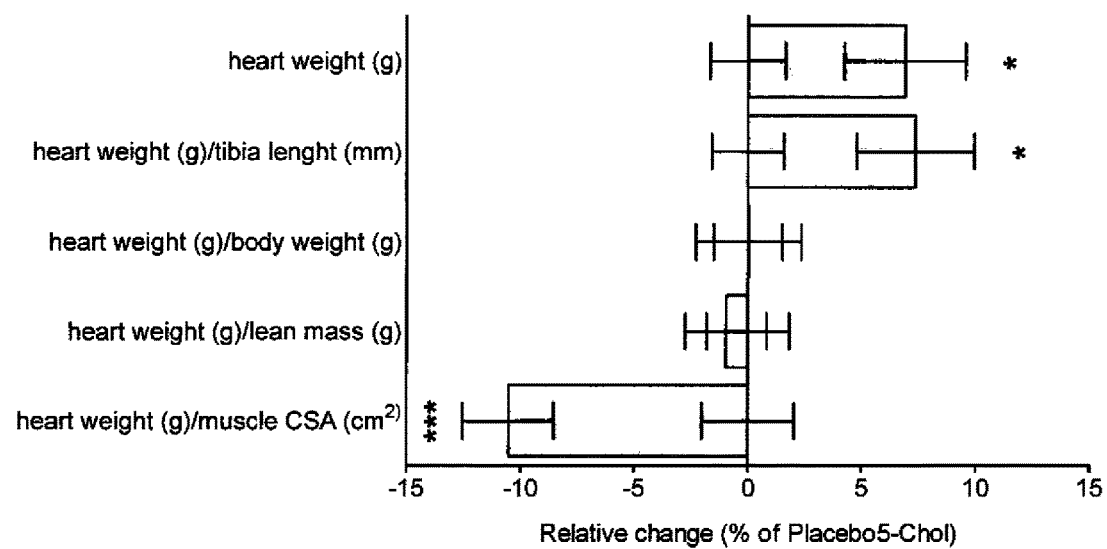
FIG. 6: Heart weight measurements normalized to different parameters for Placebo 5-chol and Mstn:1169 siRNA-conjugate. Mstn:1169 siRNA-conjugate (50 mpk) was injected intravenously into CD-1 mice (n=12), in addition to PBS and Placebo 5 cholesterol conjugate non-targeting control. Hearts were weighed and normalized to a variety of parameters (i.e., tibia length, body weight, lean mass, and muscle cross sectional area (CSA)) after 21 days of Mstn knockdown to assess signs of cardiac hypertrophy. Filled in bars indicate a statistical significant change in the specified parameter between Mstn siRNA-cholesterol conjugate and Placebo 5-cholesterol treatment. *, P<0.05; ****, P<0.0001 (by one-way ANOVA (a-b) or two-way ANOVA (c-h))

In addition to skeletal muscle, heart has also been reported to express Mstn, although to a lesser degree (Sharma M. et al., 1999, *J. Cell Physiol.* 180:1-9). Therefore, the heart was examined for potential Mstn knockdown. Quantitative PCR indicates very low Mstn mRNA expression in the heart (Ct values, 32-35, data not shown) and, therefore, mRNA knockdown could not be determined. There are many reports of changes in heart size in rodent Mstn knockout models or in response to Mstn inhibition by small molecule or neutralizing antibodies, although observations are varied, with some reports of cardiac hypertrophy, and other reports of unchanged heart size (Artaza, J. N. et al., 2007, *J. Endocrinol.* 194:63-76; Morissette, M. R., 2006, *Circ. Res.* 99:15-24; Rodgers, B. D. et al., 2009, *J. Physiol.* 587:4873-86; Whittemore, L. A. et al., 2003, *Biochem. Biophys. Res. Commun.* 300:965-71). In order to access signs of cardiac hypertrophy after 21 days of Mstn knockdown, hearts were weighed and normalized to a variety of parameters (FIG. 6). Mstn knockdown resulted in a significant increase in heart weight. When heart weight is normalized to tibia length, a parameter anticipated to remain unchanged, mice treated with Mstn siRNA-cholesterol continue to display a significant increase in heart weight. However, if heart weight is normalized to body weight (BW) or lean mass, cardiac hypertrophy is no longer observed, suggesting that the increase in heart size is compensatory to the increased BW resulting from Mstn knockdown.

Example 4: Mechanism of Uptake of Cholesterol Conjugates in Muscle siRNA Synthesis— siRNA was synthesized as described in Example 1, supra. The sequences of two Ctnnb1 siRNAs used in this Example are indicated in Table 4 (5'-3' direction). A non-targeting control siRNA was also used (see "Placebo 5" from Examples 1 and 2, supra). The content of each column is the same as those provided in Table 3, supra.

TABLE 5

Ctnnb1 siRNA sequences

| siRNA name | Strand | 5'-position 1 nuc | Nucleotide sequence -position 2 to position 20 | Nuc position 21-3' | SEQ ID NO: |
|---|---|---|---|---|---|
| Ctnnb1: 1797 [3' Chol] | S | 6amiL-iB-omeC | omeU; fluG; omeU; omeU; fluG; fluG; fluA; omeU; omeU; fluG; fluA; omeU; omeU; omeC; fluG; omeA; fluA; fluA; omeUs | omeU-iBSup | 15 |
| | A/S | vinylP-moeT | fluU; omeU; fluC; omeG; fluA; omeA; fluU; omeC; fluA; omeA; fluU; omeC; fluC; omeA; fluA; omeC; fluA; omeG; omeUs | omeUSup | 16 |
| Ctnnb1: 1797 [5' Chol] | S | iB-omeC | omeU; fluG; omeU; omeU; fluG; fluG; fluA; omeU; omeU; fluG; fluA; omeU; omeU; omeC; fluG; fluA; fluA; fluA; omeUs | omeU-iBSup | 17 |
| | A/S | vinylP-moeT | fluU; omeU; fluC; omeG; fluA; omeA; fluU; omeC; fluA; omeA; fluU; omeC; fluC; omeA; fluA; omeC; fluA; omeG; omeUs | omeUSup | 16 |

Animals—

Female C57BL/6J wild-type LDL receptor −/− and ApoE −/− mice were obtained from Jackson Laboratory (Stock #002207, 002052, respectively) and were between 25-27 weeks old at time of study. Female CD-1 mice were obtained from Charles River and were between 8-9 weeks old at time of study. All mice were maintained on a 12-hour light and dark cycle with al libitum access to water and standard chow diet (no. 5001; LabDiet). Control and experimental cholesterol-conjugated siRNAs were administered to mice by tail vein injections at indicated dosages. Blood was collected by cardiac puncture at the time of harvest. Tissue samples were collected at specific time points after dosing. All animal studies were conducted at Merck Research Laboratories in an AAALAC-accredited West Point, Pa. animal facility using protocols approved by the Institutional Animal Care and Use Committee (IACUC).

Results—

Figures 7A, 7B:
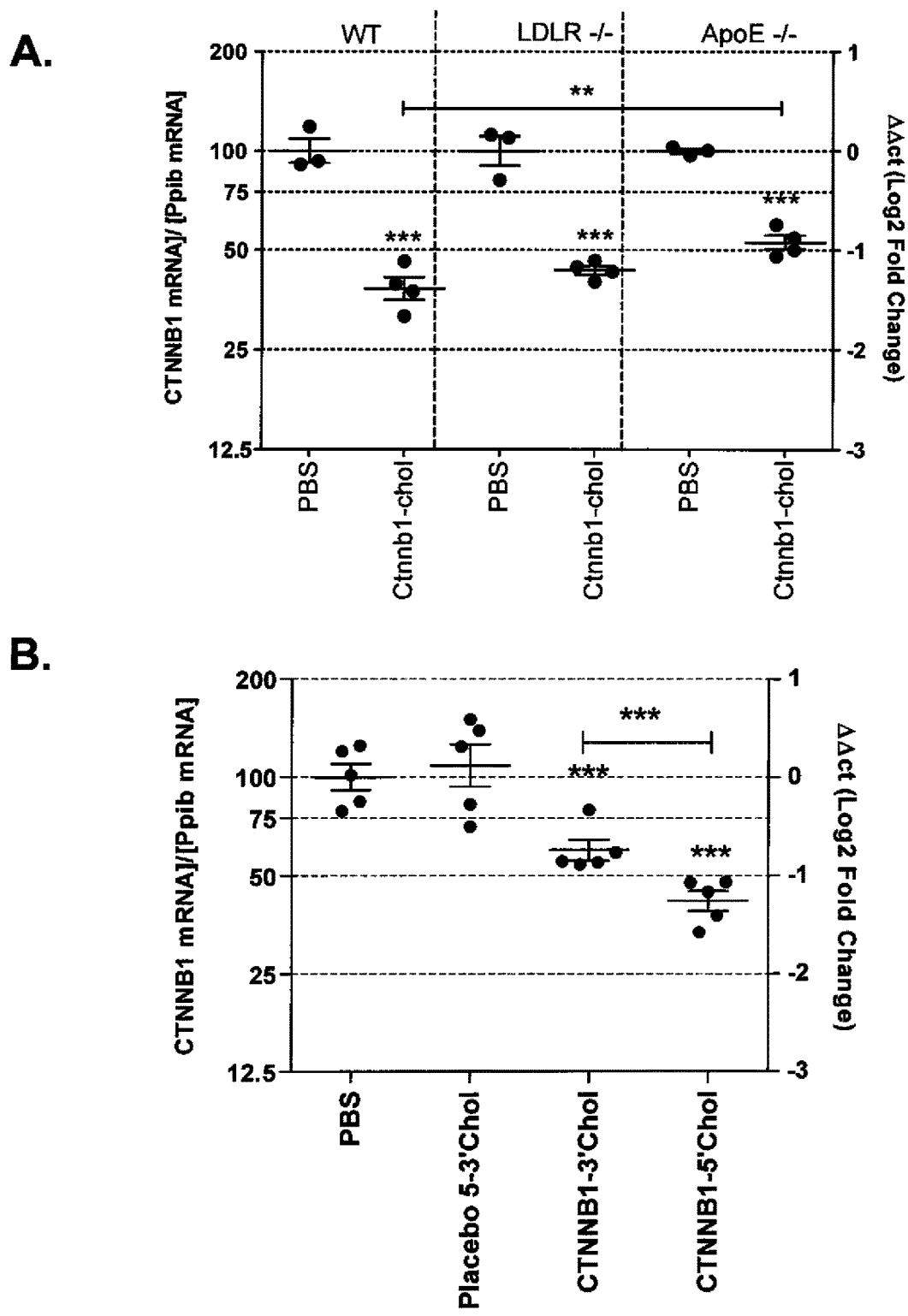
FIG. 7: Ctnnb1-chol conjugates. (A) In vivo comparison of efficacy of Ctnnb1-chol conjugates in WT, LDLR-/-, and ApoE-/- mice. Ctnnb1-chol siRNA was screened in CD-1 mice (n=3 or 4) at a 14 mpk dose by i.v. injection. Ctnnb1 mRNA expression was determined based on ΔΔCt calculations, relative to PBS, in gastrocnemius muscle 3 days post-injection. , P<0.01; *, P<0.001 (by one-way ANOVA) (B) Ctnnb1-chol siRNAs with a single cholesterol attached at either the 3' or 5' end of the passenger strand, were screened in CD-1 mice (n=5) at a 15 mpk dose by i.v. injection. Ctnnb1 mRNA expression was compared to PBS and Placebo 5 non-targeting control (3' chol). mRNA expression was determined based on ΔΔCt calculations, relative to PBS, in gastrocnemius muscle 3 days post-injection. ***, P<0.001 (by one-way ANOVA).

In order to examine the potential mechanism of uptake of cholesterol conjugates in muscle and whether association of the conjugate with lipoprotein particles is required for uptake, the efficacy of Ctnnb1 siRNA molecules with a single cholesterol entity attached to either the 3' or 5' end of the passenger strand was examined in wildtype, LDL receptor (LDLR) −/− and ApoE −/− mice. Mice were treated with a single i.v. injection of Ctnnb1:1797[3' Chol] siRNA at 14 mpk and Ctnnb1 mRNA was measured in the gastrocnemius muscle after 72 hours (FIG. 7A). A maximum of 60% mRNA knockdown was observed in wt mice. There is a reduction in mRNA KD in ApoE −/− mice (50% KD) and a trend toward reduced KD in LDLR −/− mice. The data suggests that Ctnnb1 cholesterol conjugate uptake is only partially mediated through the LDL receptor or via any ApoE-containing lipoprotein in muscle.

In order to determine whether the position of the cholesterol on the passenger strand is essential for cholesterol conjugate efficacy, Ctnnb1-chol conjugates with cholesterol on either the 3' or 5' end of the passenger strand were examined in vivo (FIG. 7B). CD-1 mice were treated with 15 mpk of either version of Ctnnb1-chol and compared to a PBS control and a Placebo 5-chol, which has cholesterol at the 3' position. Ctnnb1 mRNA levels were examined in gastrocnemius muscle 72 hours after injection. The data suggests that both positions can be used to create highly efficacious cholesterol conjugates in muscle.

Example 5: Chemical Structures of the Chemically-Modified Nucleotides Used to Generate the siRNA Molecules Exemplified Herein TABLE 6a Structure of 5'-position 1 nucleotides contained within siRNA molecules in Tables 3 and 5.

| 5'-position 1 nuc | Structure |
|---|---|
| vinylPmoeT | 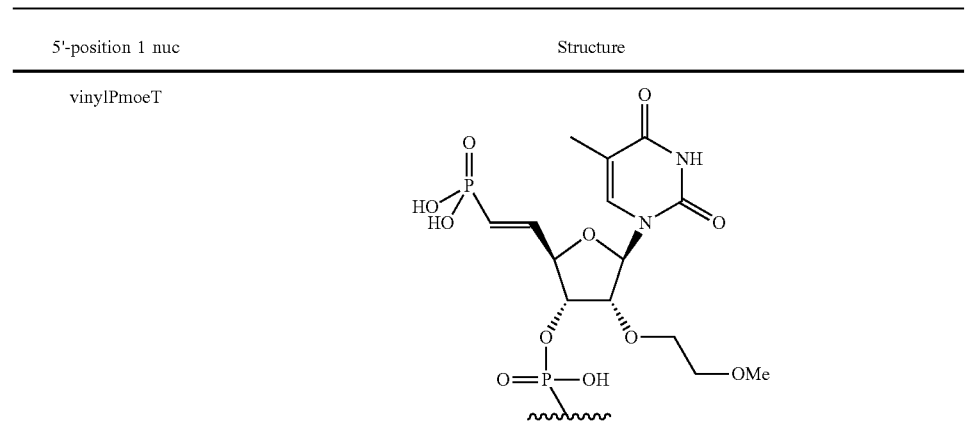 |

TABLE 6a-continued

Structure of 5'-position 1 nucleotides contained within siRNA molecules in Tables 3 and 5.

| 5'-position 1 nuc | Structure |
|---|---|
| 6amil-iB-fluX<br>X = B = Base U, G, C, A | 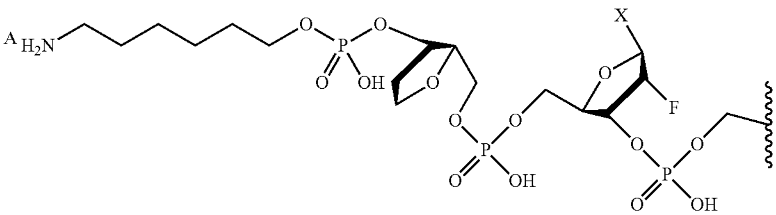 |
| 6amil-iB-omeX<br>X = B = Base U, G, C, A | 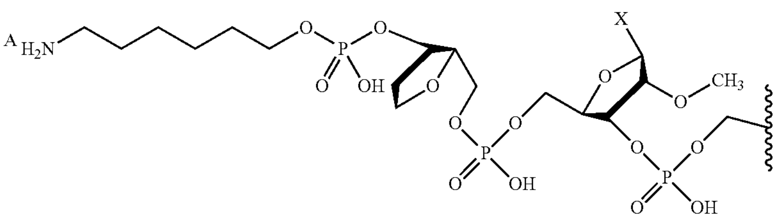 |

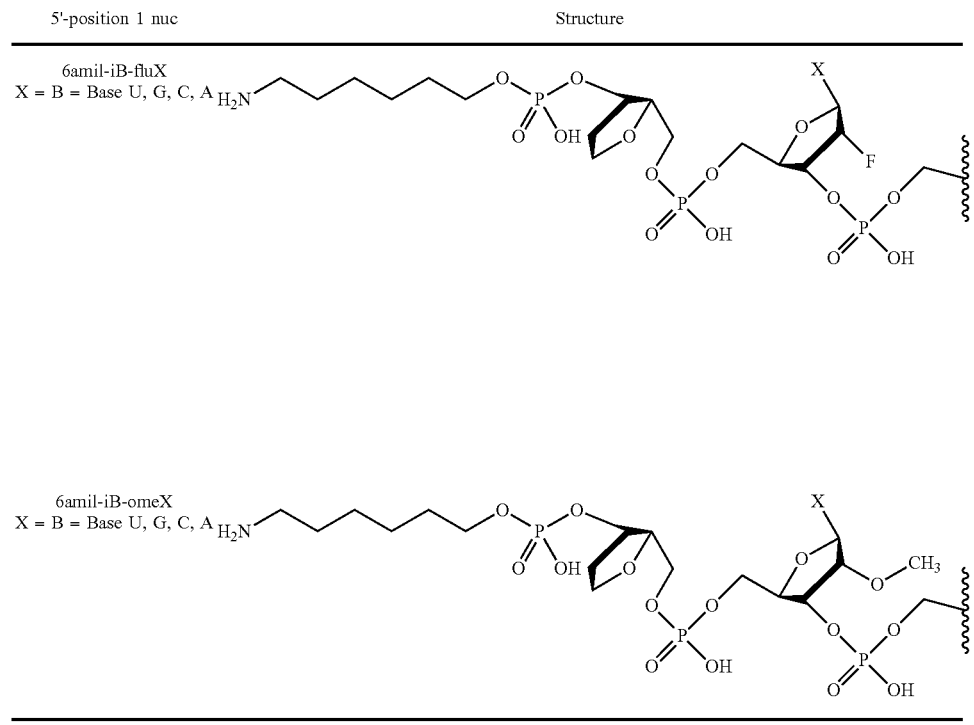

TABLE 6b

Structure of internally-located nucleotides (i.e., positions 2-20) contained within the siRNA molecules in Tables 3 and 5.

| Internal nuc (positions 2-20) | Structure |
|---|---|
| omeX<br>X = B = Base U, G, C, A | |
| omeXs<br>X = B = Base U, G, C, A | |

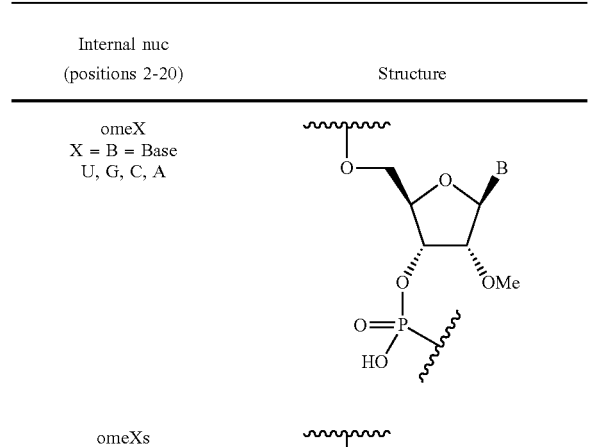

TABLE 6b-continued

Structure of internally-located nucleotides (i.e., positions 2-20) contained within the siRNA molecules in Tables 3 and 5.

| Internal nuc (positions 2-20) | Structure |
|---|---|
| fluX<br>X = B = Base U, G, C, A | |
| fluXs<br>X = B = Base U, G, C, A | |

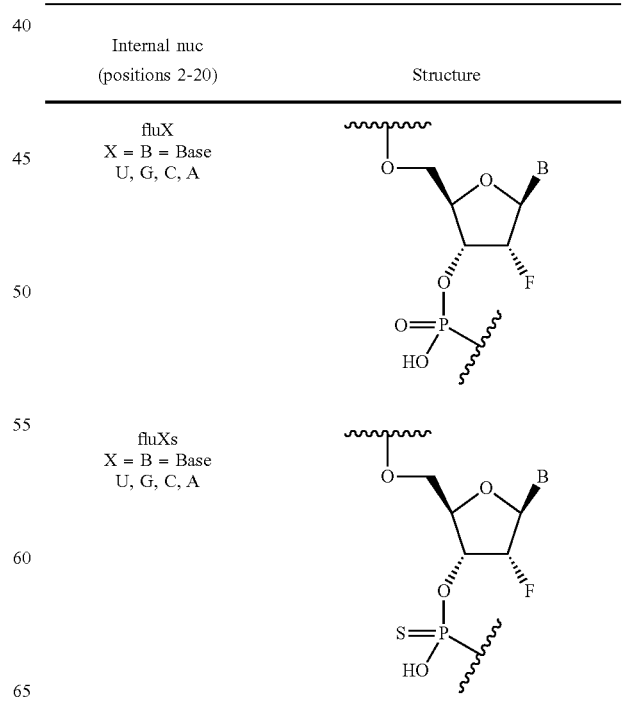

TABLE 6c

Structure of nucleotide position 21-3' nucleotides exemplified in Tables 3 and 5.

| Nuc position 21-3' | Structure |
|---|---|
| omeU-Sup | 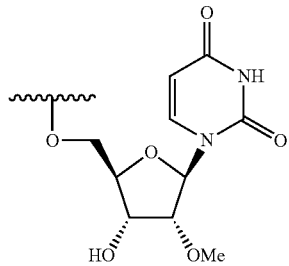 [SMILES: *OC[C@H]1O[C@@H](n2ccc(=O)[nH]c2=O)[C@H](OC)[C@@H]1O] |
| omeU-iBSup | 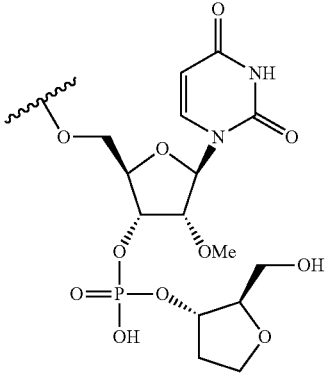 [SMILES: *OC[C@H]1O[C@@H](n2ccc(=O)[nH]c2=O)[C@H](OC)[C@@H]1OP(=O)(O)O[C@H]1CCO[C@@H]1CO] |

TABLE 6d

Structure of cholesterol CpG

| Name | Structure |
|---|---|
| Cholesterol CpG | 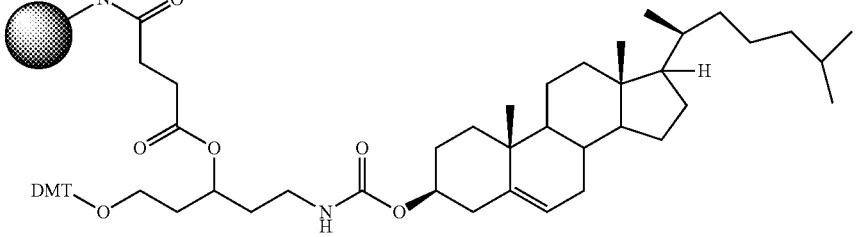 |

What is claimed is:

1. A double-stranded short interfering nucleic acid (siNA) molecule that inhibits the expression of myostatin, wherein:
   (a) the siNA comprises a sense strand and an antisense strand;
   (b) each strand is independently 19 to 30 nucleotides in length; and
   (c) the antisense strand comprises nucleotide sequence of:

(SEQ ID NO: 18)
   5'- AUUAUUUGUUCUUUGCCAU -3';

and wherein one or more of the nucleotides are chemically modified.

2. A double-stranded siNA molecule of claim 1, wherein the siNA molecule comprises:

(SEQ ID NO: 1)
   5'- AUGGCAAAGAACAAAUAAU -3'
   and (SEQ ID NO: 18)
   5'- AUUAUUUGUUCUUUGCCAU -3'.

3. The double-stranded siNA molecule of claim 2, wherein the siNA molecule is linked to a lipophilic moiety.

4. The double-stranded siNA molecule of claim 3, wherein the lipophilic moiety is cholesterol.

5. The double-stranded siNA molecule of claim 4, wherein the lipophilic moiety is attached to a 3'-end of the siNA molecule.

6. The double-stranded siNA molecule of claim 4, wherein the lipophilic moiety is attached to a 5'-end of the siNA molecule.

7. The double-stranded siNA molecule of claim 2, which comprises one or more chemically-modified nucleotides.

8. The double-stranded siNA molecule of claim 2, which comprises one or more 3'-overhanging nucleotides on one or both strands.

9. The double-stranded siNA molecule of claim 1, wherein the siNA molecule is linked to a lipophilic moiety.

10. The double-stranded siNA molecule of claim 9, wherein the lipophilic moiety is cholesterol.

11. The double-stranded siNA molecule of claim 10, wherein the lipophilic moiety is attached to a 3'-end of the siNA molecule.

12. The double-stranded siNA molecule of claim 10, wherein the lipophilic moiety is attached to a 5'-end of the siNA molecule.

13. The double-stranded siNA molecule of claim 1, which comprises one or more chemically-modified nucleotides.

14. The double-stranded siNA molecule of claim 1, which comprises one or more 3'-overhanging nucleotides on one or both strands.

* * * * *

SEQUENCE LISTING

<160> NUMBER OF SEQ ID NOS: 21

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
auggcaaaga acaaauaau                                              19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
ggcaaagaac aaauaauau                                              19

```
<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
acuccagaau agaagccau                                                       19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
uuuggaagau gacgauuau                                                       19

<210> SEQ ID NO 5
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
```

```
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 5
auggcaaaga acaaauaauu u                                          21

<210> SEQ ID NO 6
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
```

```
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 6
tuuauuuguu cuuugccauu u                                             21

<210> SEQ ID NO 7
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
```

```
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 7
ggcaaagaac aaauaauauu u                                        21

<210> SEQ ID NO 8
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
```

```
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 8
tuauuauuug uucuuugccu u                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
```

```
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 9
acuccagaau agaagccauu u                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
```

```
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
```

-continued

<223> OTHER INFORMATION: phosphorothioate internucleotide linkage

<400> SEQUENCE: 10
tuggcuucua uucuggaguu u                                            21

<210> SEQ ID NO 11
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature

```
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 11
uuuggaagau gacgauuauu u                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
```

```
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 12
tuaaucguca ucuuccaaau u                                              21

<210> SEQ ID NO 13
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
```

```
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 13
gucgccuuau aucggucgau u                                      21
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
```

```
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 14
tcgaccgaua uaaggcgacu u                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: aminohexyl phosphate inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
```

```
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 15
cuguuggauu gauucgaaau u                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal vinyl phosphate
<220> FEATURE:
<221> NAME/KEY: misc_feature
<222> LOCATION: (1)..(1)
<223> OTHER INFORMATION: 2'-methoxyethoxy
<220> FEATURE:
<221> NAME/KEY: misc_feature
<222> LOCATION: (2)..(21)
<223> OTHER INFORMATION: ribonucleotide unmodified or modified as
      described for this sequence
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
```

```
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate internucleotide linkage

<400> SEQUENCE: 16
tuucgaauca auccaacagu u                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2-deoxy-2'-fluoro
<220> FEATURE:
<221> NAME/KEY: misc_feature
<222> LOCATION: (20)..(21)
<223> OTHER INFORMATION: 2'-O-methyl
```

```
<220> FEATURE:
<221> NAME/KEY: misc_feature
<222> LOCATION: (20)..(21)
<223> OTHER INFORMATION: phosphorothioate internucleotide linkage
<220> FEATURE:
<221> NAME/KEY: misc_feature
<222> LOCATION: (21)..(21)
<223> OTHER INFORMATION: inverted abasic cap

<400> SEQUENCE: 17 cguuggauu gauucgaaau u                                          21

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
auuauuuguu cuuugccau                                            19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
auauuauuug uucuuugcc                                            19

<210> SEQ ID NO 20
<211> LENGTH: 19
<212> TYPE: RNA
<213> ORGANISM: Artificial Sequence
<220> FEATURE:
<223> OTHER INFORMATION: Synthetic

<400> SEQUENCE: 20
auggcuucua uucuggagu                                            19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
auaaucguca ucuuccaaa                                            19
```